(12) United States Patent
Ibrahim et al.

(10) Patent No.: US 11,230,533 B2
(45) Date of Patent: Jan. 25, 2022

(54) CRYSTALLINE SALTS AND POLYMORPHS OF A P2X3 ANTAGONIST

(71) Applicant: Afferent Pharmaceuticals, Inc., San Mateo, CA (US)

(72) Inventors: Prabha Ibrahim, San Mateo, CA (US); Ronald Charles Hawley, San Mateo, CA (US); Anthony P. Ford, Palo Alto, CA (US); Steven A. Smith, San Mateo, CA (US)

(73) Assignee: AFFERENT PHARMACEUTICALS, INC., San Mateo, CA (US)

( * ) Notice: Subject to any disclaimer, the term of this patent is extended or adjusted under 35 U.S.C. 154(b) by 0 days.

(21) Appl. No.: 16/863,070

(22) Filed: Apr. 30, 2020

(65) Prior Publication Data

US 2020/0255386 A1 Aug. 13, 2020

Related U.S. Application Data

(63) Continuation of application No. 16/468,992, filed as application No. PCT/US2017/066562 on Dec. 15, 2017.

(60) Provisional application No. 62/436,533, filed on Dec. 20, 2016.

(51) Int. Cl.
*C07D 239/48* (2006.01)
*A61K 9/20* (2006.01)
*A61K 31/191* (2006.01)

(52) U.S. Cl.
CPC .......... *C07D 239/48* (2013.01); *A61K 9/2095* (2013.01); *A61K 31/191* (2013.01)

(58) Field of Classification Search
CPC ... C07D 239/48; A61K 9/2095; A61K 31/191
See application file for complete search history.

(56) References Cited

U.S. PATENT DOCUMENTS

| | | | |
|---|---|---|---|
| 10,662,162 B2 * | 5/2020 | Hawley | ................ C07D 239/48 |
| 10,676,444 B2 * | 6/2020 | Ibrahim | ................ A61K 9/2095 |
| 10,822,311 B2 * | 11/2020 | Hawley | ..................... A61P 1/16 |
| 2008/0086004 A1 | 4/2008 | Dvorak et al. | |
| 2008/0207655 A1 | 8/2008 | Dillon et al. | |
| 2014/0357629 A1 | 12/2014 | Broka et al. | |
| 2015/0057299 A1 | 2/2015 | Ford et al. | |
| 2015/0290181 A1 | 10/2015 | Lee et al. | |
| 2017/0151241 A1 | 6/2017 | Ford et al. | |
| 2018/0271863 A1 | 9/2018 | Thevananther et al. | |
| 2018/0280388 A1 | 10/2018 | Ford et al. | |
| 2019/0055202 A1 * | 2/2019 | Hawley | .................... A61P 11/14 |
| 2019/0389811 A1 * | 12/2019 | Hawley | .................... A61P 13/10 |
| 2020/0239421 A1 * | 7/2020 | Hawley | .................... A61P 11/14 |
| 2021/0008071 A1 * | 1/2021 | Broka | .................... A61K 31/505 |
| 2021/0009531 A1 * | 1/2021 | Broka | .................... A61P 33/00 |

FOREIGN PATENT DOCUMENTS

| | | |
|---|---|---|
| WO | 2005095359 A1 | 10/2005 |
| WO | 2008040652 A1 | 4/2008 |
| WO | 2015027212 A1 | 2/2015 |
| WO | WO-2019209607 A1 * 10/2019 ........... C07D 487/08 |

OTHER PUBLICATIONS

Muccino; Pulmonary Pharmacology & Therapeutics 2019, 56, 75-78. (Year: 2019).*
Ryan; Expert Opinion on Pharmacotherapy, 2018, 19, 687-711. (Year: 2018).*
Wang; PNAS, 2018, 115, 4939-4944. (Year: 2018).*
"In pursuit of P2X3 antagonists: novel therapeutics for chronic pain and afferent sensitization", Purinergic Signalling, Kluwer Academic Publishers, Do, vol. 8, No. Suppl 11, Feb. 2012, pp. S3-S26, XP002699076, ISSN: 1573-9546, DOI: 10.1007/S11302-011-9271-6.
Abdulqawi, R. et al., P2X3 receptor antagonist (AF-219) in refractory chronic cough: a randomised, double-blind, placebo-controlled phase 2 study, Lancet, 2015, 1198-1205, 385.
Ford, Anthony P. et al., The therapeutic promise of ATP antagonism at P2X3 receptors in respiratory and urological disorders, Frontiers in Cellular Neuroscience, 2013, 1-10, 7(267).
International Search Report and Written Opinion for PCT/US2017/066562, dated Dec. 15, 2017, 12.
Poloni, Laura N. et al., Site Discrimination and Anisotropic Growth Inhibition by Molecular Imposters on Highly Dissymmetric Crystal Surfaces, Cryst. Growth Des., 2016, 5525-5541, 16.
Balbach, S. et al., Pharmaceutical evaluation of early development candidates "The 100 mg approach", International Journal of Pharmaceutics, 2004, 1-12, 275.
Singhal, Dharmenda, et al., Drug polymorphism and dosage form design: a practical perspective, Advanced Drug Delivery Reviews, 2004, 335-347, 56.
Berge, S.M., et al.,, "Pharmaceutical Salts", J. Pharm. Sci, 1977, pp. 1-19, vol. 66, No. 1.
Caira, Crystalline Polymorphism of organic compounds, Topics in Current Chemistry, 1998, 163-208, 198.
Akhapkina, V.I. et al., Fundamental principles of the modulatory concept and classification of modulatory drugs, RMJ, 2012, 933-951, 19.
Bastin, R.J.; et al., Salt Selection and Optimization Procedures for Pharmaceutical New Chemical Entities, Organic Process Research and Development, 2000, pp. 427-435, 4.
Bernstein, J., Bioavailability, Polymorphism of molecular crystals, 2007, 324-330 (translated pp. 1-9), Ch. 7.3.2.
Bernstein, J., Bioavailability, Polymorphism of molecular crystals, 2007, 324-330, Ch. 7.3.2.
Kummerer, K., Pharmaceuticals in the environment, Annual Review of Environment and Resources, 2010, 57-75, 35.

(Continued)

Primary Examiner — Daniel R Carcanague
(74) Attorney, Agent, or Firm — Yong Zhao; Catherine D. Fitch

(57) ABSTRACT

Provided are novel salts and polymorphs of 5-(2,4-diamino-pyrimidin-5-yloxy)-4-isopropyl-2-methoxy-benzenesulfonamide, which are potentially useful for modulating a condition mediated by a P2X3 or P2X2/3 receptor. Also provided are pharmaceutical formulations and methods of administration and dosing of these salts and polymorphs to subjects in need thereof.

19 Claims, 17 Drawing Sheets

(56) References Cited

OTHER PUBLICATIONS

Kuznetsova, G.A., Methodological instructions, Irkutsk State University (Seihveisu), Department of General Physics, 2005, 1, N/A.
Kuznetsova, G.A., Methodological instructions, Irkutsk State University (Seihveisu), Department of General Physics, 2005, 1-2, N/A.
Morissette, Sherry L. et al., High-throughput crystallization: polymorphs, salts, co-crystals and solvates of pharmaceutical solids, Advanced Drug Delivery Reviews, 2004, 275-300, 56.
Serajuddin, ATM, Salt formation to improve drug solubility, Advanced Drug Delivery Reviews, 2007, pp. 603-616, 59.

* cited by examiner

Indexing results for XRPD file 735063 collected with Cu-Kα radiation

| Bravais Type | Triclinic |
|---|---|
| a [Å] | 9.951 |
| b [Å] | 16.303 |
| c [Å] | 16.801 |
| α [deg] | 104.45 |
| β [deg] | 99.26 |
| γ [deg] | 103.61 |
| Volume [Å³/cell] | 2,494.5 |
| Chiral Contents? | Achiral |
| Extinction Symbol | P – |
| Space Group(s) | P1 (1), P1̄ (2) |
| Source | Manual Input |

Top to Bottom:

Compound A Free Base Form A + anhydrous citric acid (dry grind)
Compound A Free Base Form A reference pattern
Anhydrous citric acid reference pattern

CRYSTALLINE SALTS AND POLYMORPHS OF A P2X3 ANTAGONIST

CROSS REFERENCE TO RELATED APPLICATIONS

The present application is a continuation of application Ser. No. 16/468,992, filed Jun. 12, 2019, which is a 371 national phase application of International Application No. PCT/US2017/066562, filed Dec. 15, 2017, which claims the benefit of U.S. Provisional Application No. 62/436,533, filed Dec. 20, 2016, hereby incorporated by reference in their entirety.

BACKGROUND OF THE INVENTION

The present disclosure relates to crystalline forms of 5-(2,4-diamino-pyrimidin-5-yloxy)-4-isopropyl-2-methoxy-benzenesulfonamide ("Compound A") or a salt thereof.

The respiratory tract, or airways, participates in the vital process of gas exchange in order to support the demand for oxygen intake and carbon dioxide elimination. Vagal autonomic nerves control smooth muscles of the tracheobronchial tree, and thus caliber of airways, as well as liberation and movement of secretions (mucus and fluid). Control is coordinated within brainstem nuclei which regulate voluntary and autonomic outflow, relying on a rich input of vagal sensory signals from the airway tissues that in turn convey conscious sensation and trigger autonomic reflexes. Vagal sensory fibers arise mostly from cell bodies within jugular and nodose ganglia, and their activity is regulated by a range of chemical substances such as ATP, which sensitizes vagal afferents and serves as a convergent mechanosensory airways signal.

ATP activates purinoceptors (e.g., P2X3 and P2X2/3), which mediate many physiological and pathological roles. ATP stimulates and sensitizes sensory nerve endings resulting in intense sensations such as pain, discomfort, urgency, itch and urge and a pronounced increase in sensory nerve discharge, largely via P2X3 receptor activation on afferent nerve fibers innervating rodent and human tissues and organs, especially the hollow viscera.

Compound A is described in International Publication WO2005/095359 (published on Oct. 13, 2005) and U.S. Pat. No. 7,858,632 (published Sep. 22, 2005), which are hereby incorporated by reference in their entireties. Compound A is a P2X3 and/or P2X2/3 inhibitor and is potentially useful for the treatment of cough, chronic cough and urge to cough in respiratory conditions and disorders, among other conditions.

SUMMARY OF THE INVENTION

Disclosed herein are salt forms and polymorphs of Compound A. In one embodiment, the polymorph is a crystalline free base Form A of Compound A. In another embodiment, the polymorph is a crystalline citrate salt Form A of Compound A. In another embodiment, the polymorph is a crystalline citrate salt Form B of Compound A. In another embodiment, the polymorph is a crystalline tartrate salt Form A of Compound A. In yet another embodiment, the polymorph is a crystalline tartrate salt Form F of Compound A.

DETAILED DESCRIPTION OF THE INVENTION

Disclosed herein are novel salts and crystalline forms of Compound A, an inhibitor of P2X3 and/or P2X2/3 receptor(s). Compound A, 5-(2,4-diamino-pyrimidin-5-yloxy)-4-isopropyl-2-methoxy-benzenesulfonamide, has the following formula:

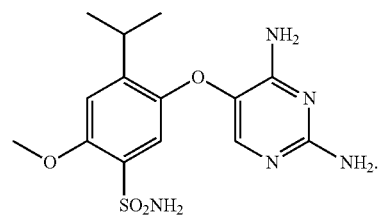 [SMILES: COc1cc(C(C)C)c(Oc2cnc(N)nc2N)cc1S(N)(=O)=O]

Compound A can be prepared using procedures described in International Publication WO2005/095359 (published on Oct. 13, 2005), U.S. Pat. No. 7,858,632 (published Sep. 22, 2005) and U.S. Pat. No. 7,741,484 (published Mar. 1, 2007).

The novel crystalline forms of Compound A or a salt thereof, especially the citrate salt Form A, tartrate salt Form A and tartrate salt Form F, described herein, can be provided stably and constantly from the standpoint of the manufacturing process, and are useful in the potential treatment of P2X3 and/or P2X2/3 mediated conditions. These crystalline polymorphs have many unexpected properties as compared to the free base forms as described in more detail below.

In one embodiment, the crystalline polymorphs described herein have improved properties when compared to other forms.

The novel crystalline forms of Compound A disclosed herein have a P2X3 and/or P2X2/3 inhibitory effect, and are therefore potentially useful as pharmaceutical agents for the treatment of conditions or disorders including, but not limited to, the urinary tract (aka uropathy) disorders, disease states associated with the urinary tract (aka urinary tract disease states), overactive bladder (aka detrusor hyperactivity or urge incontinence), outlet obstruction (aka benign prostatic hypertrophy), outlet insufficiency, pelvic hypersensitivity, bladder pain syndrome, endometriosis, respiratory symptoms, cough or urge to cough associated with a respiratory disease, asthma, hypertension, heart failure, dyspnea (aka shortness of breath), sleep apnea, signs and symptoms of carotid body hypertonicity and hyperreflexia (such as breathlessness and fatigue), and sympathetic overactivity in a subject. Additionally, signs and symptoms of upper respiratory tract infection, including the cold and flu symptoms of pharyngitis, rhinitis, nasal congestion, hypertussivity, rhinorrhea and sneezing targeted conditions can potentially be treated by compound A disclosed herein.

In particular, the novel crystalline forms of Compound A or a salt thereof, as well as Compound A per se, are potentially useful as pharmaceutical agents, for example, for the treatment of respiratory symptoms, cough or urge to cough associated with a respiratory disease, and asthma.

X-ray powder diffraction (XRPD) studies are widely used to characterize molecular structures, crystallinity, and polymorphism. The XRPD patterns of the novel polymorphs disclosed herein were generated on a PANalytical X'Pert PRO MPD diffractometer using an incident beam of Cu radiation produced using an Optix long, fine-focus source. More detailed XRPD conditions are described in the Examples section.

Figure 1:
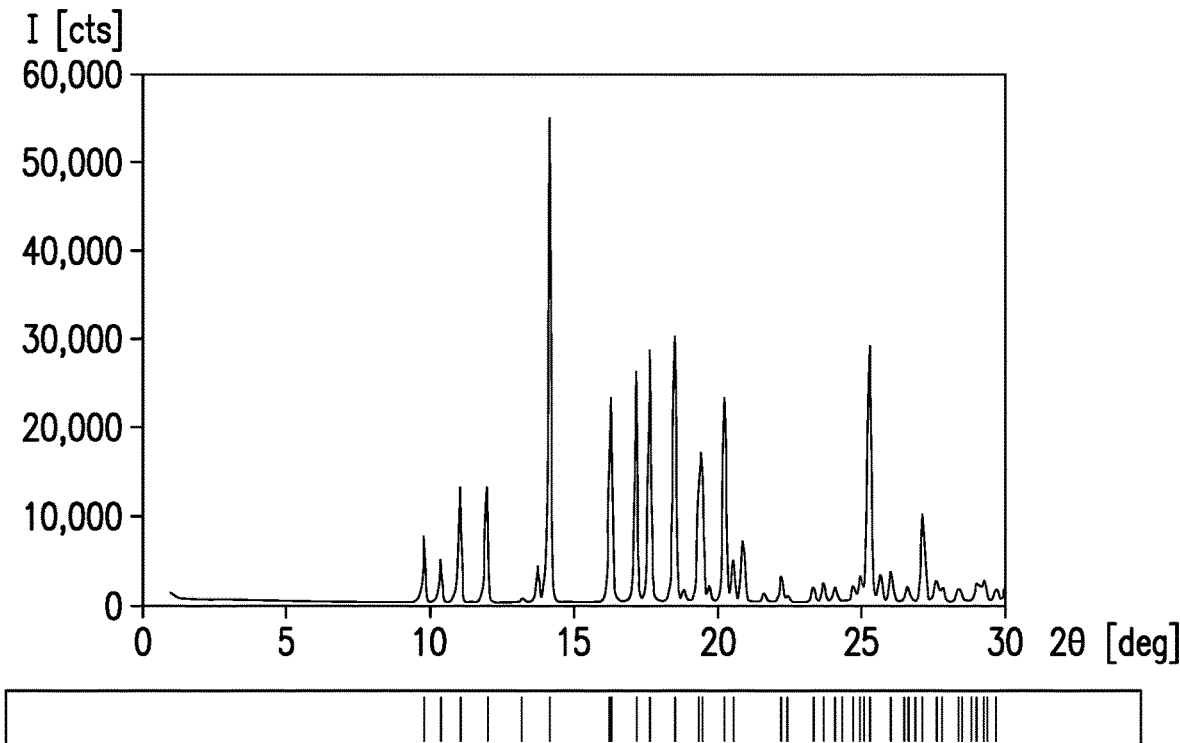
FIG. 1 is a characteristic XRPD pattern for Compound A free base Form A.

The XRPD pattern of the free base Form A of Compound A is shown in FIG. 1. This material can be used as the starting material for making other forms as described in more detail in the Examples section.

Figure 3:
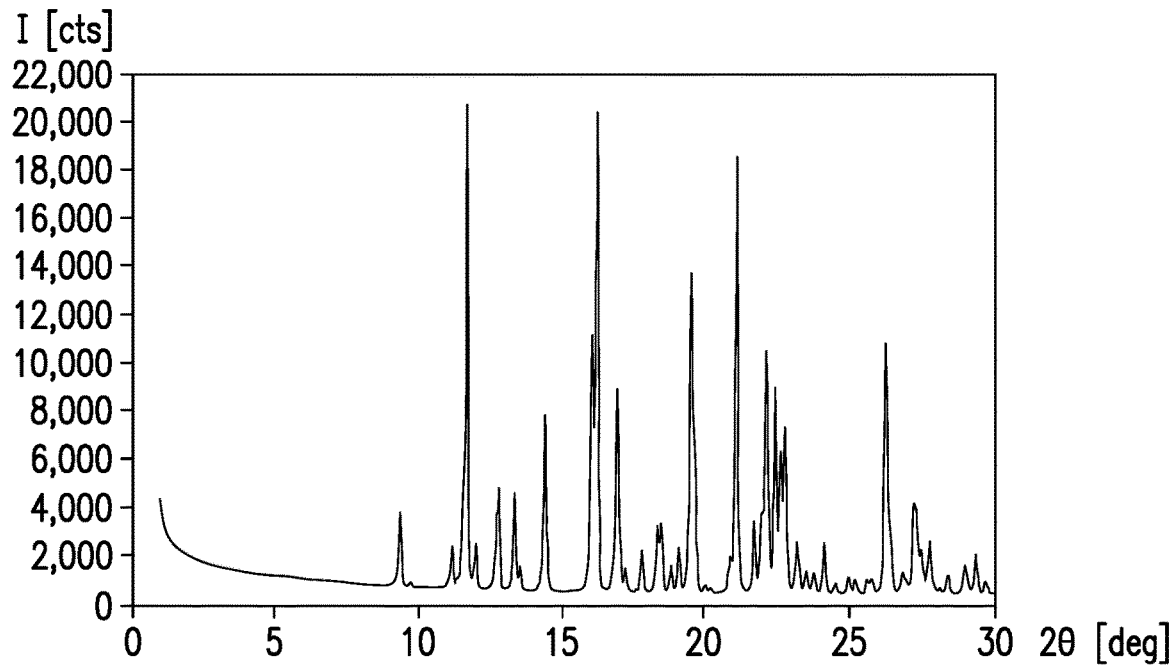
FIG. 3 is a characteristic XRPD pattern for citrate salt Form A of Compound A.

In one embodiment, the XRPD pattern of a citrate salt Form A of Compound A is shown in FIG. 3. In one embodiment, the citrate Form A exhibits characteristic diffraction peaks corresponding to d-spacings of 11.69, 16.22 and 21.14 angstroms. In another embodiment, the citrate Form A is further characterized by the d-spacings of 9.38 and 26.31 angstroms. In another embodiment, the citrate Form A is even further characterized by the d-spacings of 14.41 and 19.51 angstroms. In another embodiment, the citrate Form A is still further characterized by the d-spacings of 16.95 and 22.18 angstroms.

In one embodiment, the XRPD pattern of citrate Form A exhibits characteristic diffraction peaks corresponding to d-spacings of 9.38, 11.69, 14.41, 16.22, 16.95, 19.54, 21.14, 22.18 and 26.31 angstroms.

In addition to the XRPD pattern described above, the citrate Form A was also characterized by proton nuclear magnetic resonance (NMR) spectra. In one embodiment, the proton NMR data indicated a 1:1 Compound A to citrate ratio.

Figure 4:
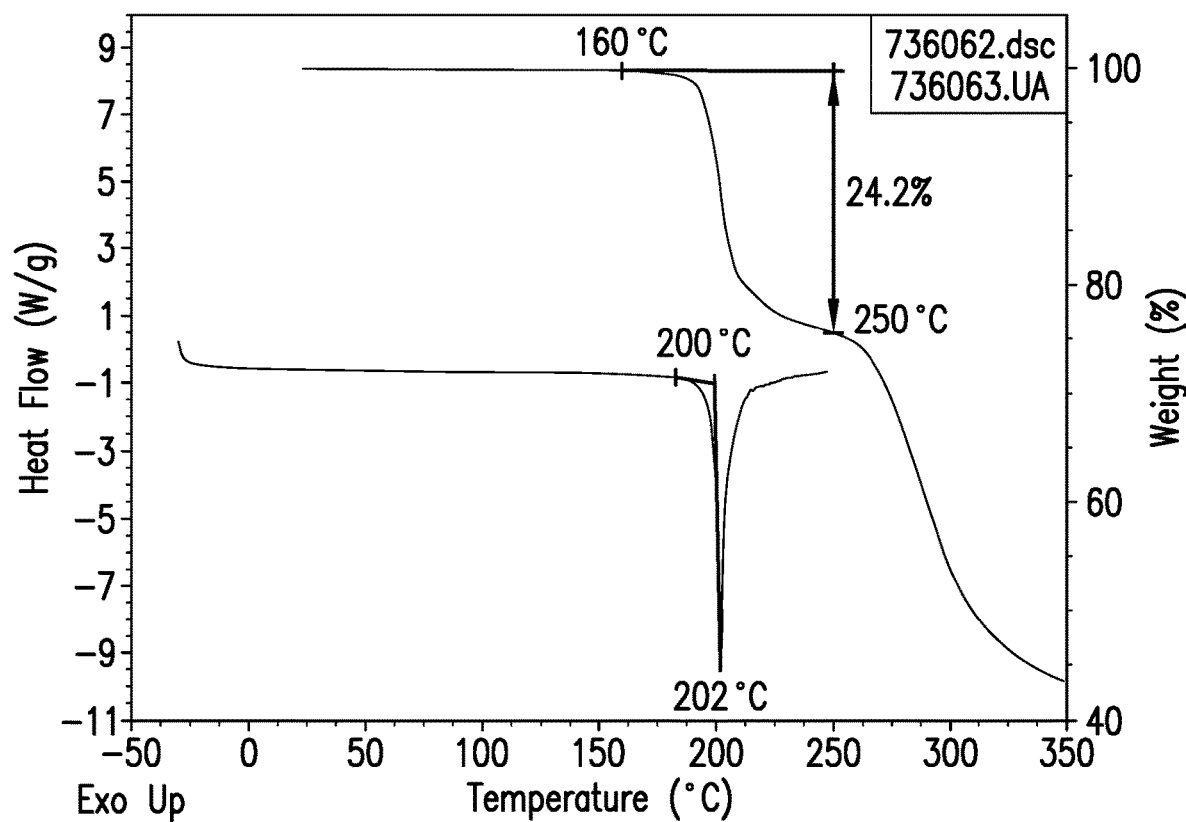
FIG. 4 is a DSC and TGA overlay for citrate salt Form A of Compound A.

Citrate Form A was further characterized using DSC (Differential Scanning calorimetry) and TGA (Thermogravimetric Analysis). In one embodiment, the DSC/TGA thermograms for citrate Form A is shown in FIG. 4. Negligible weight loss was observed by TGA up to 160° C., consistent with an anhydrous/nonsolvated material. Stepwise weight loss of about 24 wt % between 160° C. and 250° C. and an endothermic event by DSC with an onset of 200° C., likely indicating concurrent melting and decomposition of the material.

In one embodiment, hot stage images for citrate Form A confirmed a melt onset at approximately 193° C., slightly lower than the melt onset marked in the DSC thermogram in FIG. 4 (200° C.).

Figure 5:
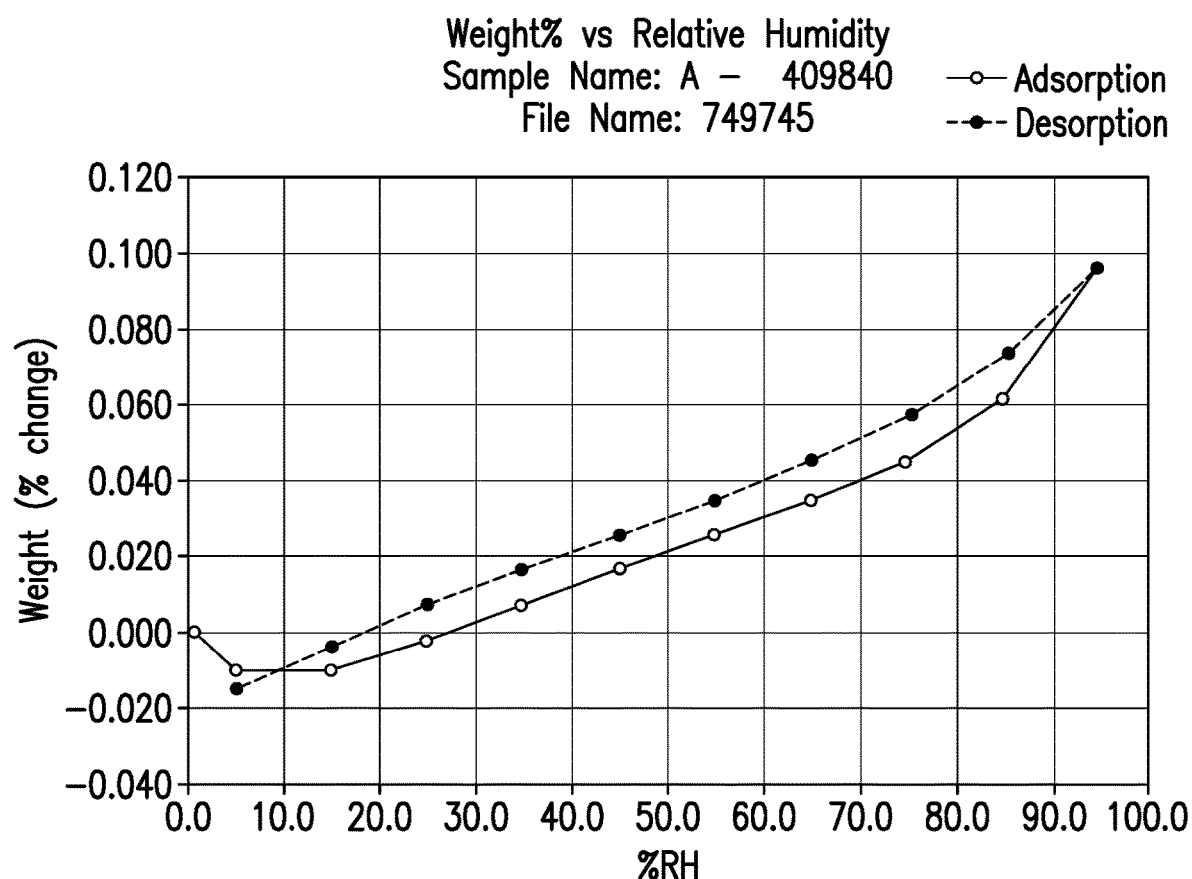
FIG. 5 is a DVS isotherm for citrate salt Form A of Compound A.

Citrate Form A was further characterized by DVS (Dynamic Vapor Sorption) analysis. In one embodiment, the DVS isotherm, shown in FIG. 5, illustrated low kinetic hygroscopicity (0.11% total weight gain/loss between 5% and 95% RH).

Citrate Form A has unexpected properties as compared to the free base Form A. In one embodiment, citrate Form A exhibited improved aqueous solubility as compared to free base Form A and showed no signs of disproportionation at the 6 mg/mL concentration for upto a month. Additionally, no deliquescence was noted upon stressing the salt at ~97% relative humidity for 14 days.

Figure 6:
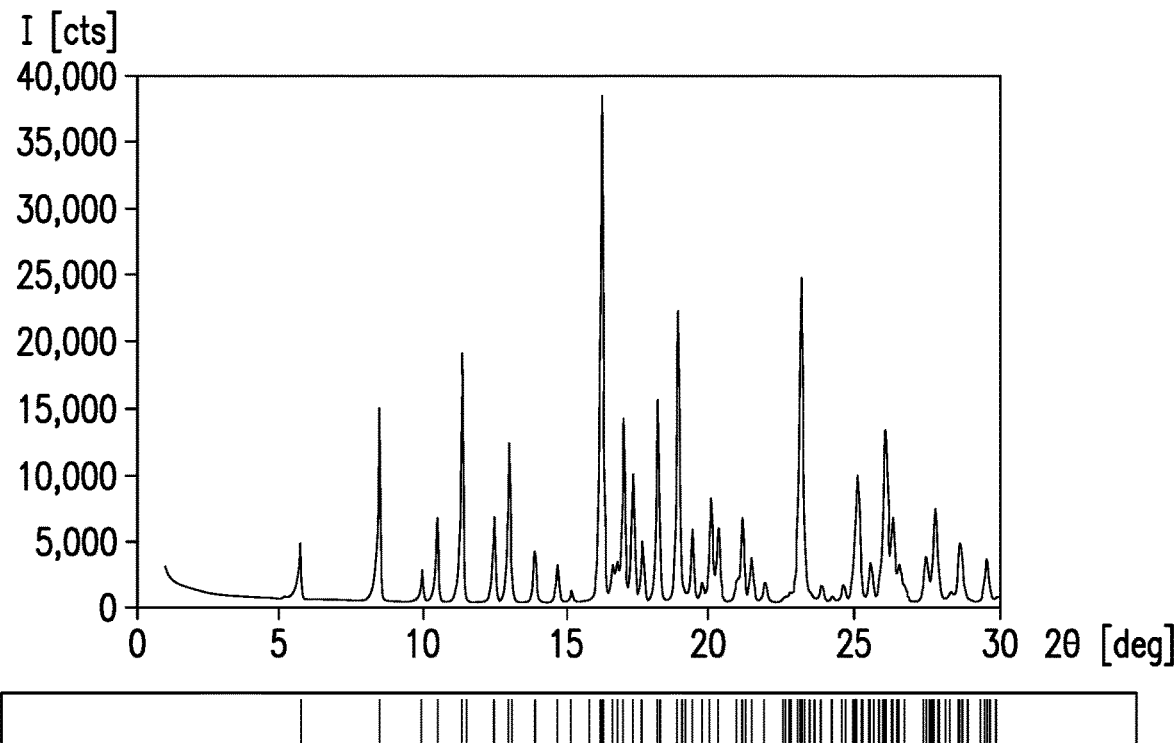
FIG. 6 is a characteristic XRPD pattern for citrate salt Form B of Compound A.

In one embodiment, the XRPD pattern of a citrate salt Form B of Compound A is shown in FIG. 6. In one embodiment, the citrate Form B exhibits characteristic diffraction peaks corresponding to d-spacings of 8.42, 16.15 and 23.04 angstroms. In another embodiment, the citrate Form A is further characterized by the d-spacings of 5.71 and 18.77 angstroms. In another embodiment, the citrate Form A is even further characterized by the d-spacings of 11.30 and 26.01 angstroms. In another embodiment, the citrate Form A is still further characterized by the d-spacings of 12.93 and 25.02 angstroms.

In one embodiment, the XRPD pattern of citrate Form B exhibits characteristic diffraction peaks corresponding to d-spacings of 5.71, 8.42, 11.30, 12.93, 16.15, 18.77, 23.04, 25.02 and 26.01 angstroms.

In one embodiment, proton NMR of the citrate Form B indicated a 1:1 Compound A and citrate salt ratio with only minor residual ethanol present. Any water that may be present could not be quantitated by proton NMR due to the inherent presence of water in the NMR solvent (deuterated DMSO).

In one embodiment, Karl Fischer analysis indicated that a sample containing citrate Form B contained approximately 3 wt % water. This amount of water correlates with a monohydrate of a 1:1 citrate salt.

Figure 7:
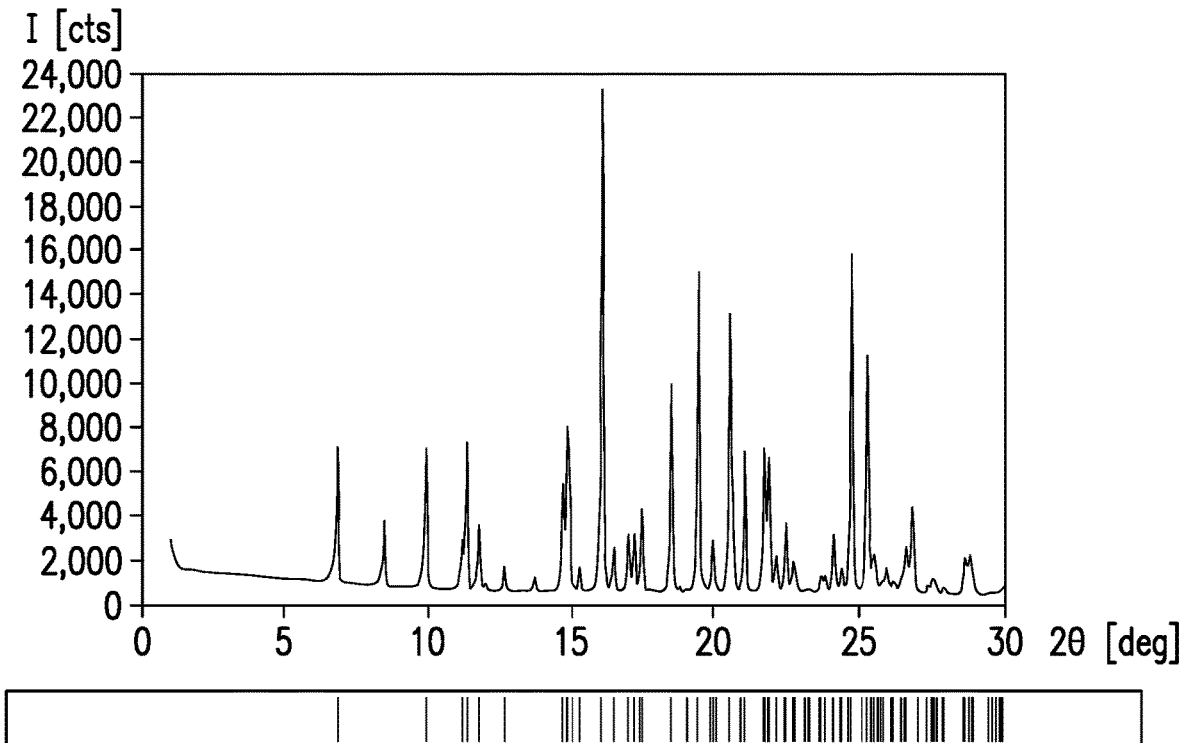
FIG. 7 is a characteristic XRPD pattern for tartrate salt Form A of Compound A.

In one embodiment, the XRPD pattern of a tartrate salt Form A of Compound A is shown in FIG. 7.

In one embodiment, a proton NMR spectrum for tartrate Form A indicated a 2:1 salt with 0.4 mole EtOH per mole of Compound A, suggesting a ~2:1:1 Compound A/acid/EtOH stoichiometry.

Figure 8:
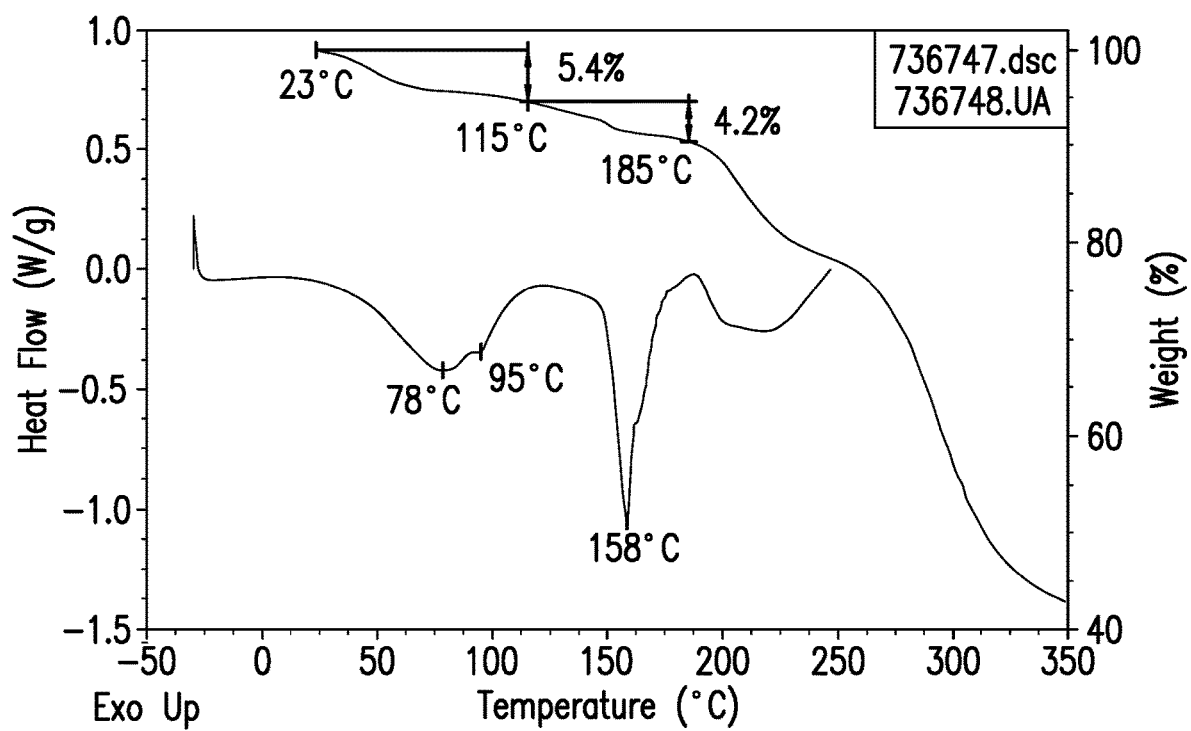
FIG. 8 is a DSC and TGA overlay for tartrate salt Form A of Compound A.

In one embodiment, an overlay of the DSC and TGA thermograms for tartrate Form A is shown in FIG. 8. A broad endotherm with a peak maximum at 78° C. and a shoulder peak at 95° C. in the DSC thermogram corresponds with about 5% weight loss between 23 and 115° C. by TGA, consistent with the loss of solvent. The magnitude of weight loss is consistent with ~1 mole EtOH per mole of 2:1 Compound A tartrate salt, consistent with the amount of EtOH measured by proton NMR. An additional weight loss step of about 4 wt % corresponds with an endothermic event with a peak maximum at 158° C., likely corresponding with concurrent melting, dissociation, and decomposition of the salt.

Figure 11:
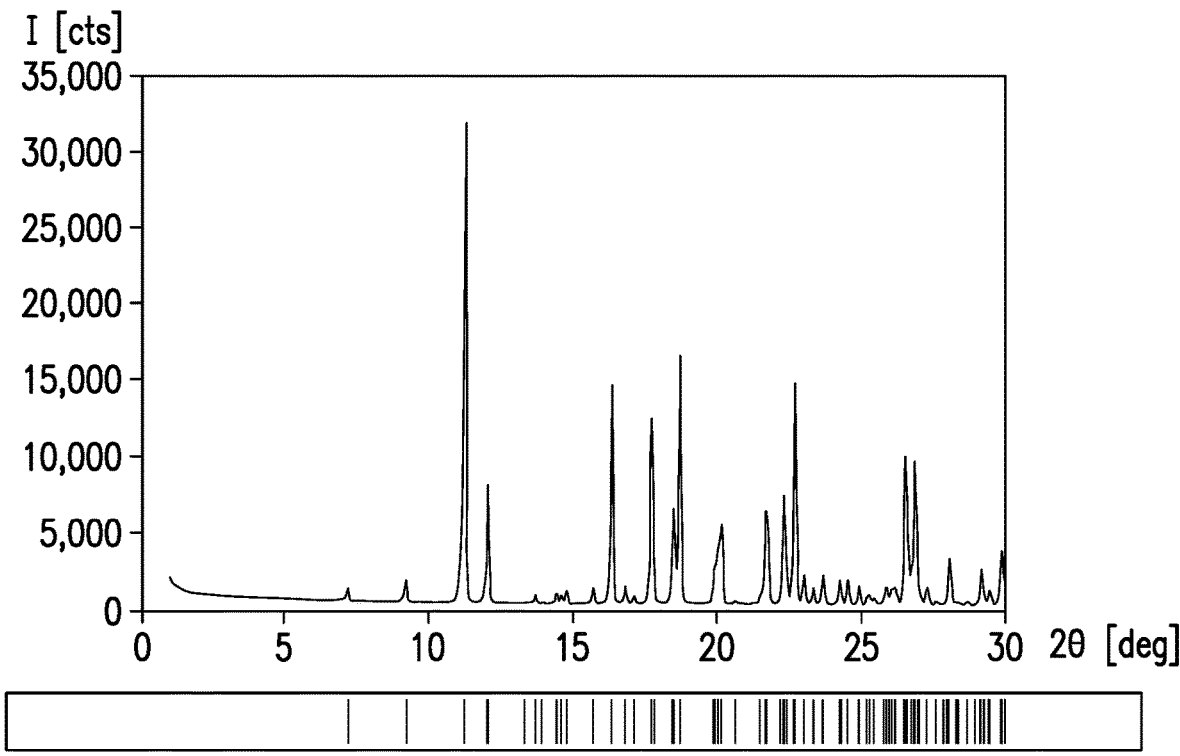
FIG. 11 is a characteristic XRPD pattern for tartrate salt Form F of Compound A.

In one embodiment, the XRPD pattern of a tartrate salt Form F of Compound A is shown in FIG. 11. In one embodiment, the tartrate Form F exhibits characteristic diffraction peaks corresponding to d-spacings of 11.25, 18.73, and 22.67 angstroms. In another embodiment, the tartrate Form F is further characterized by the d-spacings of 12.06 and 17.74 angstroms. In another embodiment, the tartrate Form F is even further characterized by the d-spacings of 9.22 and 26.52 angstroms. In another embodiment, the tartrate Form F is still further characterized by the d-spacings of 16.37 and 21.69 angstroms.

In one embodiment, the XRPD pattern of tartrate Form F exhibits characteristic diffraction peaks corresponding to d-spacings of 9.22, 11.25, 12.06, 16.37, 17.74, 18.73, 21.69, 22.67 and 26.52 angstroms.

In addition to the XRPD pattern described above, the tartrate Form F was also characterized by proton nuclear magnetic resonance (NMR) analysis. In one embodiment, a proton NMR spectrum indicated a 2:1 Compound A tartrate salt.

Tartrate Form F was further characterized by DSC and TGA. In one embodiment, an overlay of the DSC and TGA thermograms for tartrate Form F is presented in FIG. 12. An initial weight loss step of about 6.6 wt % between 27-100° C. by TGA corresponds with a broad endotherm by DSC at 125° C., likely corresponding with the loss of solvent. The weight loss equates to ~3 moles water per mole of 2:1 salt, consistent with the amount of water allowed by the unit cell volume. Virtually no weight loss is noted between 100-180° C. A relatively sharp endotherm at 179° C. is immediately followed by steep weight loss above 180° C., likely indicating concurrent melting and decomposition of the dehydrated material.

In one embodiment, hot stage photomicrographic analysis for tartrate Form F illustrate changes in birefringence noted between 70° C. and 98° C., corresponding with the stepwise weight loss and broad endotherm noted in the TGA and DSC data that likely indicate dehydration of the sample upon heating. Melting was observed between ~171° C. and 176° C., confirming that the sharp DSC endotherm at onset 173° C. corresponds with the melt of the dehydrated material.

In one embodiment, Karl Fischer analysis of tartrate Form F indicated about 7.3% water, equivalent to approximately 3.7 moles water per mole of 2:1 salt. This water content is slightly higher than the ~3 moles of water indicated by the TGA weight loss.

Figure 13:
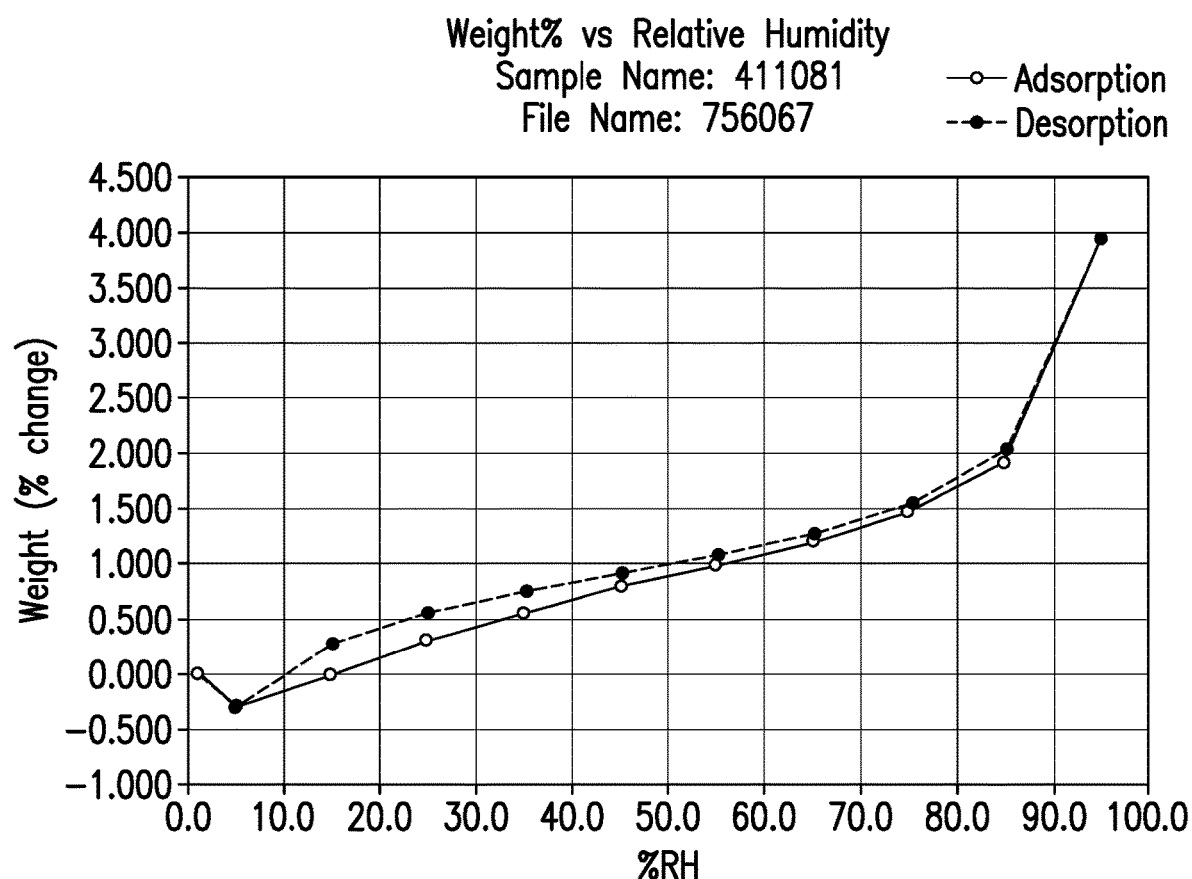
FIG. 13 is a DVS isotherm for tartrate salt Form F of Compound A.

In one embodiment, a DVS isotherm for tartrate Form F is shown in FIG. 13. The material exhibited relatively small weight loss upon equilibration to 5% RH (0.29 wt %), indicating that the hydrate likely remained intact at the start of adsorption. Significant hygroscopicity was noted between 5% and 95% RH, with the sample gaining a total of about 4.23 wt %. Approximately half of the weight gain occurred gradually between 5% and 85% RH, while the other half occurred during the single step between 85% and 95% RH.

Although significant weight gain was observed from the DVS experiment, the hydrated material showed no signs of deliquescence at ~97% RH during the screen. The desorption profile mirrors the sorption profile with very little hysteresis observed. Total weight loss of about 4.25 wt % occurred between 95% and 5% RH, with approximately half of the weight loss occurring in one step between 95% and 85% RH. XRPD of the post-DVS sample indicated no form change.

Tartrate Form F exhibited improved aqueous solubility by solvent addition as compared to Compound A free base Form A, although disproportionation in neat water was observed to begin after 1 day.

EXAMPLES

Example 1: Preparation of Free Base Form A of Compound A

Step 1. Preparation of Sulfonic Acid Compound

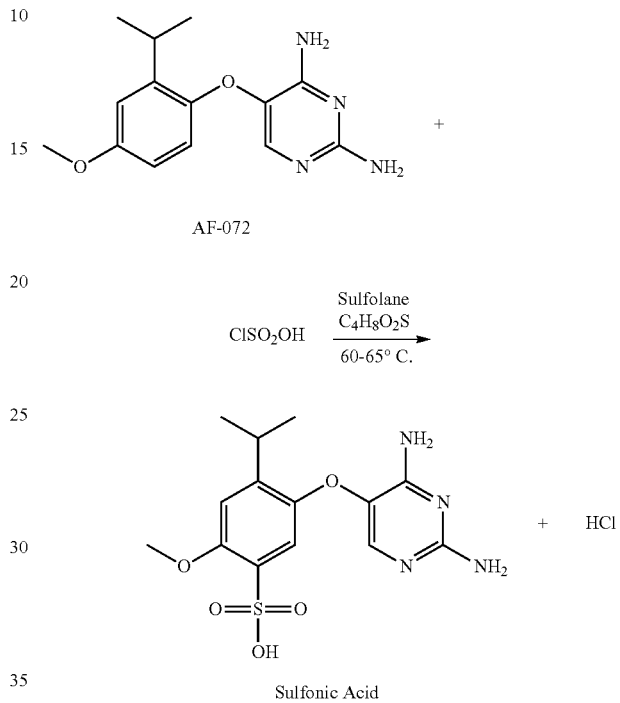

AF-072 and sulfolane were charged separately to the reactor and the temperature was adjusted to 50-55° C. Chlorosulfonic acid was added slowly maintaining the temperature between 50-62° C. to begin the sulfonation reaction. The temperature was adjusted to 58-62° C. and held for 4 hours before taking a sample for reaction completion. A kicker charge of chlorosulfonic acid can be used if necessary.

Step 2. Preparation of Sulfonal Chloride Compound

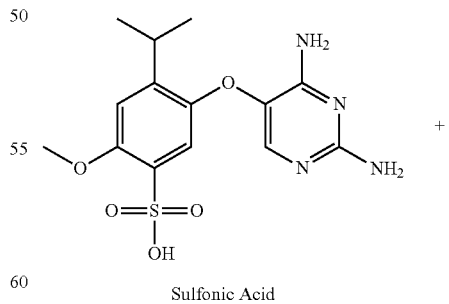

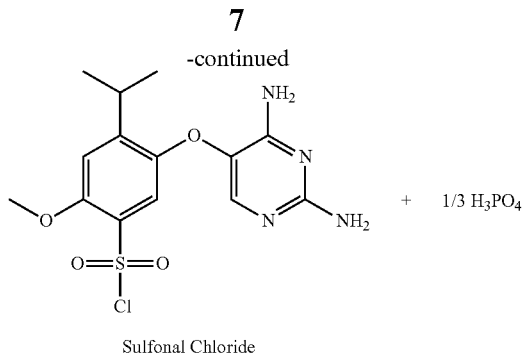

Sulfonal Chloride

The batch from Step 1 was adjusted to 65-70° C. and then phosphorous oxychloride was charged maintaining a temperature between 60-70° C. The batch was adjusted to 73-77° C. and held for 17 hours before taking a sample for reaction completion. The sample was taken after an additional 3 hours of holding. A kicker charge of phosphorous oxychloride can be used if necessary.

Step 3. Preparation of Compound A

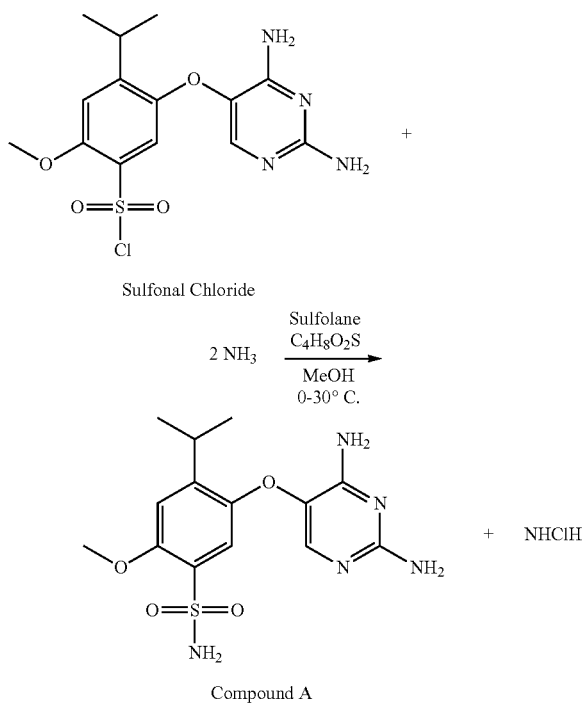

Methanol was charged to another vessel and cooled to between −10° C. and 0° C. Anhydrous ammonia was charged to the methanol slowly, maintaining a temperature below 0° C. The methanol ammonia solution was adjusted to 0-5° C. after the charge was complete. The chlorination reaction solution was transferred into the methanolic ammonia solution while maintaining the temperature between 0-30° C. Sulfolane was used to chase the transfer line, and then the batch was adjusted to 18-22° C. and held for 2.5 hours. In addition to the formation of crude Compound A, the methanolic ammonia also acts to quench residual chlorosulfonic acid, phosphorous oxychloride, and phosphoric acid, to form water-soluble salts that are removed during isolation.

Following quench completion, the batch was distilled under vacuum with tempered water on the jacket to remove the methanol and residual ammonia. Water was charged to the batch, and then the temperature was adjusted to 93-97° C. and held for 1 hour. The batch was cooled over approximately 13 hours to 18-22° C. and the product was isolated on the centrifuge to give Compound A wet cake.

Step 4. Distillation and Isolation of Compound A

The contents from Step 3 were cooled to 0-10° C. Vacuum was pulled on the contents in order to distill and remove the methanol and ammonia. The distillation was started at 5.4° C. and heating was continued for approximately 8 hours until the batch temperature reached 67.7° C. At this point the distillate stopped coming over, showing that all the methanol and ammonia have been removed. Once the distillation was stopped the batch was adjusted to 60-70° C.

In a separate reactor water was charged and heated to 60-70° C. The material was then transferred from to another reactor while maintaining a temperature of 60-70° C. At this point water was added, heated to 60-70° C. and transferred to another unit. The unit was then heated to 93-97° C. and held for 2 hours. After this hold was completed, the crystallization cool down was started. The material was then cooled to 20° C. over approximately 12 hours, and held for 1 hour.

The material was then centrifuged. Once all the material was transferred to the centrifuge, a 14 gallon chase was transferred through the slurry piping in order to recover product left behind. Centrifuging took approximately 6 hours altogether, and a wetcake was isolated from the unit. The material was then dried in the drying area resulting in Compound free base Form A.

Free base Form A of Compound A was used as the starting material for obtaining other salts and forms.

Example 2: Characterization of Free Base Form A of Compound A

Free base Form A was characterized by XRPD and proton NMR spectroscopy. The XRPD pattern (FIG. 1) exhibited sharp peaks consistent with a crystalline material and was successfully indexed. The unit cell volume obtained from the indexing solution is consistent with anhydrous/non-solvated Compound A. A proton NMR spectrum for the material is consistent with the chemical structure of Compound A free base.

A salt screen utilizing free base Form A was conducted and resulted in the salts and polymorphs described in more detail below.

Solubility estimates (by solvent addition) for Compound A free base Form A in various solvents are provided in Table 1. Solubilities are calculated based on the total solvent used to give a solution; actual solubilities may be greater because of the volume of the solvent portions used or a slow rate of dissolution. Values are rounded to the nearest whole number. If dissolution did not occur as determined by visual assessment, the value is reported as "<".

TABLE 1

Approximate Solubilities of Compound A Free Base Form A in Various Solvents

| Solvent | Solubility (mg/mL) |
| --- | --- |
| acetone | <1 |
| ACN | <2 |
| DMSO | 20 |
| EtOAc | <1 |
| EtOH | <1 |

TABLE 1-continued

Approximate Solubilities of Compound A
Free Base Form A in Various Solvents

| Solvent | Solubility (mg/mL) |
|---|---|
| MeOH | 1 |
| TFE | 2 |
| water | <1 |
| acetone/water 50:50 (v/v) | <1 |
| ACN/water 90:10 (v/v) | 1 |

Example 3: Free Base Form B of Compound A

Figure 2:
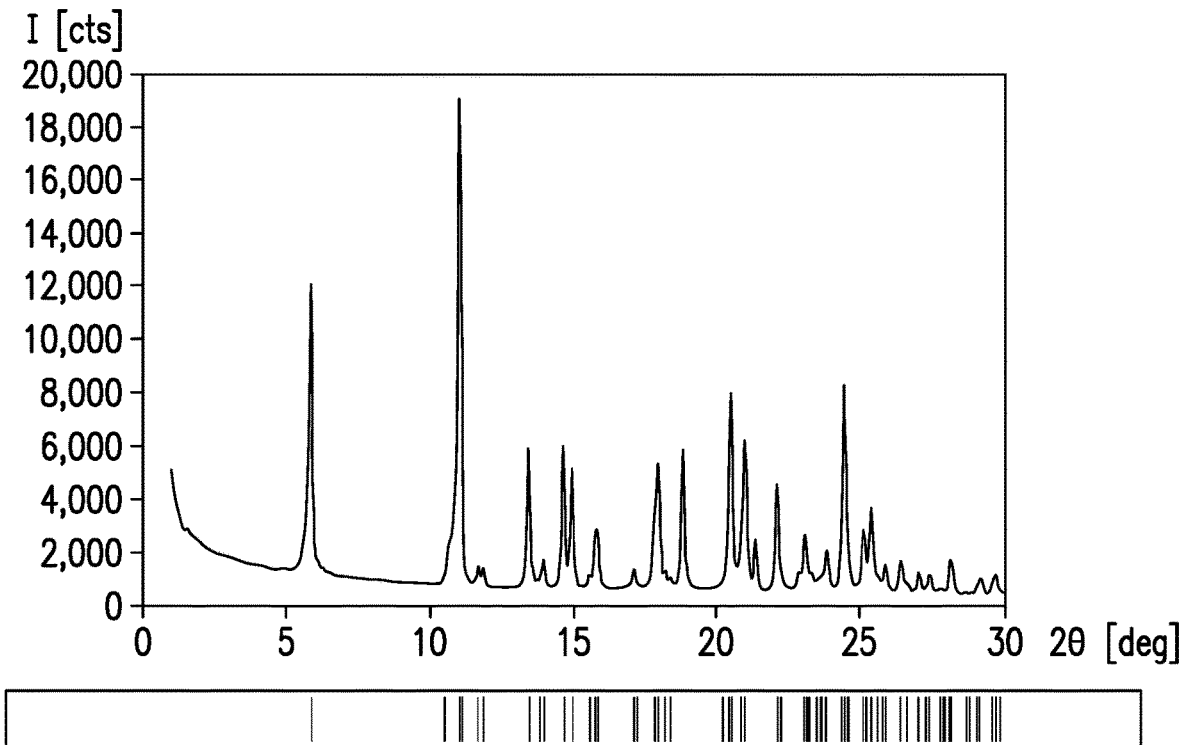
FIG. 2 is a characteristic XRPD pattern for Compound A free base Form B.

Free Base Form B may consist of an acetone solvate of Compound A free base, although the chemical composition was not confirmed. The XRPD pattern (FIG. 2) was successfully indexed, confirming that the sample consists primarily or exclusively of a single crystalline phase. The unit cell volume obtained from the indexing solution can accommodate up to ~1 mole of acetone per mole of Compound A free base.

Example 4: Salt Screen of Compound A

Salt screens were set up using free base Form A and citric acid and L-tartaric acid, respectively. The screen began by combining Compound A free base and selected acids in a 1:1 molar ratio. Due to the low solubility of the free base, most experiments involved the addition of acid (either as solids or a solution) to a slurry of free base. In some experiments, clear or nearly clear solutions were achieved upon contact, followed by precipitation, indicating salt formation. Detailed experimental conditions for obtaining citrate and tartrate salts are listed in Table 2.

As used in Table 2, the molar ratio is given as API/acid and the API is Compound A free base Form A. The temperatures (° C.) reported for DSC are transition maxima unless otherwise stated and are rounded to the nearest degree. The weight loss (%) reported for TGA at a certain temperature is rounded to 1 decimal place.

TABLE 2

Salt Screen of Compound A Using Free Base Form A as Starting Material

| API/Acid Molar Ratio | Conditions | Technique | Results |
|---|---|---|---|
| citric acid 1:1 | 1) add EtOH to API and acid solids w/stirring 2) slurry, RT, 1 day 3) vac. filter | Obs  OM XRPD | 1) cloudy suspension 2) opaque white suspension 3) white solids  fines and aggregates, B/E Citrate Form A + FB Form A |
| citric acid 1:1.2 |  | Obs | 1) solids present 2) solids present (no change) 3) opaque white suspension 4) white solids |
|  | 1) add EtOH to API 2) add citric acid (1M, aq) w/stirring 3) slurry, RT, 1 day 4) vac. filter | OM  XRPD  DSC TGA $^1$H NMR | fines and aggregates, partial B/E Citrate Form A; pattern successfully indexed, unit cell volume consistent with 1:1 Compound A citrate salt endo 202° C. (onset 200° C.) 24.2% weight loss from 160-250° C. 1:1 citrate salt, minor residual EtOH present |
| L-tartaric acid 1:1 | 1) add acetone to API 2) add L-tartaric acid (1M, aq) w/stirring 3) slurry, RT, 1 day 4) vac. filter | Obs  OM XRPD | 1) solids present 2) soln. slowly cleared (slightly) 3) opaque white suspension 4) white solids fines and aggregates, partial B/E Likely FB Material B; pattern successfully indexed, unit cell volume consistent with solvated AF-219 FB (can accommodate up to ~1Mole acetone per mole API) |
| L-tartaric acid 1:1.5 | 1) add EtOH to API 2) add L-tartaric acid (1M, aq) w/stirring 3) slurry, RT, 1 day 4) vac. filter | Obs  OM XRPD | 1) solids present 2) soln. cleared slightly (cloudy suspension) 3) opaque white suspension 4) white solids fines and aggregates, B/E Tartrate Form A; pattern successfully indexed, unit cell volume consistent with 2:1 Compound A Tartrate salt with EtOH present (can accommodate up to ~1Mole EtOH per mole API) |

TABLE 2-continued

Salt Screen of Compound A Using Free Base Form A as Starting Material

| API/Acid Molar Ratio | Conditions | Technique | Results |
|---|---|---|---|
| | | DSC | overlapping endos 78° C. and 95° C. (peak maxima), endo 158° C. with shoulder |
| | | TGA | 5.4% weight loss from 23-115° C. 4.2% weight loss from 115-185° C. |
| | | $^1$H NMR | consistent with ~2:1:1 API/acid/EtOH solvated tartrate salt |
| L-tartaric 2:1 | 1) add EtOH to API and acid solids at ~70° C. 2) add seeds of Tartaric Material C), slurry at ~70-71° C., 1 day 3) vac. filter while warm | Obs | 1) solids present 2) opaque white suspension 3) white solids |
| | | OM | fines and aggregates, B/E |
| | | XRPD | Tartrate Form D; pattern successfully indexed, unit cell volume consistent with solvated 2:1 Compound A Tartrate salt (can accommodate up to ~1Mole EtOH per mole API) |
| | | $^1$H NMR | consistent with 2:1:1 API/acid/EtOH solvated tartrate salt |
| L-tartaric 2:1 | 1) add 2-BuOH to API and acid solids 2) add seeds of Tartaric Material C, slurry at RT, 12 days 3) vac. filter | Obs | 1) solids present 2) opaque white suspension 3) white solids |
| | | OM | fines and aggregates, B/E |
| | | XRPD | Tartaric Material E; pattern could not be indexed |
| | | $^1$H NMR | consistent with ~2:1:1 API/acid/2-BuOH solvated tartrate salt |
| L-tartaric 1:1.5 | 1) add tartaric acid (1M, aq.) to API solids w/stirring at ~50° C. 2) add additional water, stir, ~49-50° C., 2 days 3) vac. filter while warm | Obs | 1) thick suspension 2) opaque white suspension 3) white solids |
| | | OM | fines and aggregates, B/E |
| | | XRPD | Tartrate Form F; pattern successfully indexed, unit cell volume consistent with hydrated 2:1 Compound A Tartrate salt (can accommodate up to ~1.5 mole water per mole API, i.e. ~2:1:3 API/acid/water) |
| | | DSC | broad endo 125° C., sharp endo 179° C. (onset 173° C., 70 J/g) |
| | | TGA | 6.6% wt loss 27-100° C. 0.2% wt loss 100-180° C. 11.7% wt loss 180-240° C. |
| | | $^1$H NMR | consistent with 2:1 (API/acid) tartrate salt |
| | | DVS post-DVS XRPD | Tartrate Form F (no change) |

Several new materials were discovered from the first round of experiments, but excess unreacted free base was observed in many of the XRPD patterns. Excess acid (1:1.2 to 1:1.5 Compound A/acid) was added in the next round of experiments in an effort to avoid precipitation of the free base. This technique was more successful in producing new materials as a single solid phase. In general, unique materials were subjected to XRPD indexing to gauge phase purity and possible stoichiometric ratios allowed by the unit cell volume, if indexing was successful.

Select materials were additionally characterized by proton NMR to confirm the chemical composition. Certain materials of interest that were found to be solvated were dried under various conditions in an effort to produce anhydrous/non-solvated salt forms. Additionally, approximate aqueous solubility and physical stability were assessed for select salts.

From the initial screen, unique forms including citrate Form A and tartrate Forms A, D, and F were obtained.

In addition to the confirmed and potential salts found, several salt screen experiments conducted in acetone yielded a material designated as likely free base Form B. The unit cell volume obtained from the XRPD indexing solution can accommodate Compound A free base with up to 1 mole of acetone per mole of Compound A. Considering the multiple preparations, all from acetone-containing solvent systems, and the unit cell volume, the material likely consists of an acetone solvate of Compound A free base.

Multiple forms were observed for the tartrate salts. Compound A tartrate exhibited a propensity to form several solvated forms as well as a hydrate.

Tartrate Form A resulted from a salt formation experiment in EtOH using 1 M aqueous L-tartaric acid. Characterization data for tartrate Form A indicates an EtOH solvated hemi-tartrate salt. Based on this, tartrate Form A was dried under vacuum at ~66° C. for 1 day, resulting in conversion to a new material, designated as tartrate Form B, and ~9% gravimetric weight loss. Similarities in some of the XRPD peak positions with those for Form A were observed, possibly indicating partial desolation at the conditions tested, so the Form B sample was additionally dried under vacuum at ~83-86° C. for 1 day, resulting in conversion to another new material, designated tartrate Form C. As for Form B, similarities in the XRPD patterns for Form C and Form A were noted, possibly indicating incomplete drying. Form C was used as seeds for several tartrate salt formation experiments in an effort to obtain an anhydrous/non-solvated form.

Considering the propensity for the tartrate salt to exist as a solvate, several additional experiments were set up in an effort to produce an anhydrous/non-solvated tartrate salt. A salt formation experiment was conducted in EtOH at ~70° C. utilizing seeds of tartrate Form C and a 2:1 Compound A/acid molar ratio (likely the preferred stoichiometry based on characterization of previously-generated tartrate samples). The resulting slurry was allowed to stir at ~70-71° C. for 1 day, and tartrate Form D, a confirmed EtOH solvate resulted. An additional salt formation experiment in 2-BuOH was set up, also seeded with Form C, in an effort to prevent solvate formation by employing a chemically bulkier solvent. This experiment, resulted in Form E, a 2-BuOH solvated salt.

In an effort to form a hydrate of the tartrate salt, a salt formation experiment was set up in water at ~50° C. The slightly elevated temperature was employed to increase the solubility of the free base, which would likely increase the reaction kinetics and facilitate formation of a salt. A hydrated hemi-tartrate salt, designated as tartrate Form F, resulted from the experiment and was selected for further study.

Select citrate and tartrate materials were evaluated by stressing at high relative humidity and estimating the aqueous solubility at ambient temperature. Citrate Form A and tartrate Form B (dried EtOH solvate) showed no signs of deliquescence at ~97% RH after 7-14 days. Citrate Form A and tartrate Form F both showed improved aqueous solubility as compared to Compound A free base Form A by solvent addition (6 mg/mL for citrate, 2 mg/mL for tartrate, <1 mg/mL for free base). Citrate Form A showed no signs of disproportionation, maintaining a clear solution at the 6 mg/mL concentration for up to 1 month with a measured pH of ~4. Likely disproportionation was observed for the tartrate Form F solubility sample, as a small amount of white precipitate was observed after standing at ambient conditions for 1 day.

Citrate Form A (anhydrous/non-solvated 1:1 citrate salt) and tartrate Form F (hydrated 2:1 Compound A tartrate salt) were further characterized. Both materials were successfully reproduced on a ~1-1.2 g scale. Citrate Form A was produced by combining 1 M aqueous citric acid with a slurry of Compound A free base Form A in EtOH. The experiment was repeated at a ~5.6 g scale, successfully yielding citrate Form A. The resulting material was used in the abbreviated stable form screen of citrate Form A. Scale-up of tartrate Form F on a ~1 g scale was also successful by combining an aqueous solution of L-tartaric acid with free base Form A at ~51° C., seeding with tartrate Form F, and allowing the mixture to stir at ~51° C. for 1 day. The scaled-up tartrate Form F material was utilized for drying and slurry studies, described in more detail below. Detailed procedures for the scale up of both materials are given below.

Example 5: Citrate Form A of Compound A

Citrate Form A consists of an anhydrous/non-solvated 1:1 Compound A citrate salt and was reproducibly prepared by adding aqueous citric acid to a slurry of Compound A free base in EtOH and stirring for an extended duration. In one embodiment, citrate Form A was prepared using conditions listed in Table 2.

The XRPD pattern for citrate Form A of Compound A is shown in FIG. 3. Lists of observed and prominent peaks are shown in Tables 3 and 4, respectively.

TABLE 3

List of observed XRPD peaks for Citrate Form A

| °2θ | d space (Å) | Intensity (%) |
|---|---|---|
| 9.38 ± 0.20 | 9.421 ± 0.200 | 18 |
| 9.73 ± 0.20 | 9.086 ± 0.186 | 4 |
| 11.17 ± 0.20 | 7.915 ± 0.141 | 11 |
| 11.69 ± 0.20 | 7.562 ± 0.129 | 100 |
| 12.00 ± 0.20 | 7.369 ± 0.122 | 12 |
| 12.75 ± 0.20 | 6.940 ± 0.108 | 18 |
| 12.81 ± 0.20 | 6.904 ± 0.107 | 23 |
| 13.36 ± 0.20 | 6.622 ± 0.099 | 22 |
| 13.54 ± 0.20 | 6.532 ± 0.096 | 8 |
| 14.41 ± 0.20 | 6.141 ± 0.085 | 37 |
| 16.05 ± 0.20 | 5.517 ± 0.068 | 53 |
| 16.22 ± 0.20 | 5.459 ± 0.067 | 97 |
| 16.95 ± 0.20 | 5.226 ± 0.061 | 42 |
| 17.24 ± 0.20 | 5.140 ± 0.059 | 7 |
| 17.82 ± 0.20 | 4.972 ± 0.055 | 11 |
| 18.38 ± 0.20 | 4.824 ± 0.052 | 16 |
| 18.49 ± 0.20 | 4.794 ± 0.051 | 16 |
| 18.85 ± 0.20 | 4.703 ± 0.049 | 8 |
| 19.13 ± 0.20 | 4.637 ± 0.048 | 11 |
| 19.54 ± 0.20 | 4.540 ± 0.046 | 66 |
| 19.68 ± 0.20 | 4.507 ± 0.045 | 35 |
| 20.04 ± 0.20 | 4.426 ± 0.044 | 4 |
| 20.21 ± 0.20 | 4.390 ± 0.043 | 3 |
| 20.92 ± 0.20 | 4.243 ± 0.040 | 10 |
| 21.14 ± 0.20 | 4.199 ± 0.039 | 89 |
| 21.75 ± 0.20 | 4.083 ± 0.037 | 17 |
| 22.01 ± 0.20 | 4.035 ± 0.036 | 19 |
| 22.18 ± 0.20 | 4.005 ± 0.036 | 50 |
| 22.48 ± 0.20 | 3.952 ± 0.035 | 43 |
| 22.67 ± 0.20 | 3.919 ± 0.034 | 30 |
| 22.82 ± 0.20 | 3.893 ± 0.034 | 35 |
| 23.23 ± 0.20 | 3.825 ± 0.032 | 12 |
| 23.54 ± 0.20 | 3.776 ± 0.032 | 7 |
| 23.80 ± 0.20 | 3.735 ± 0.031 | 6 |
| 24.15 ± 0.20 | 3.682 ± 0.030 | 12 |
| 24.53 ± 0.20 | 3.625 ± 0.029 | 4 |
| 25.00 ± 0.20 | 3.559 ± 0.028 | 6 |
| 25.24 ± 0.20 | 3.525 ± 0.027 | 5 |
| 25.67 ± 0.20 | 3.468 ± 0.027 | 5 |
| 25.81 ± 0.20 | 3.448 ± 0.026 | 5 |
| 26.31 ± 0.20 | 3.385 ± 0.025 | 51 |
| 26.92 ± 0.20 | 3.309 ± 0.024 | 6 |
| 27.33 ± 0.20 | 3.260 ± 0.023 | 20 |
| 27.54 ± 0.20 | 3.236 ± 0.023 | 11 |
| 27.84 ± 0.20 | 3.202 ± 0.023 | 13 |
| 28.49 ± 0.20 | 3.130 ± 0.022 | 6 |
| 29.08 ± 0.20 | 3.068 ± 0.021 | 8 |
| 29.44 ± 0.20 | 3.031 ± 0.020 | 9 |
| 29.78 ± 0.20 | 2.998 ± 0.020 | 5 |

TABLE 4

List of prominent XRPD peaks for Citrate Form A

| °2θ | d space (Å) | Intensity (%) |
|---|---|---|
| 9.38 ± 0.20 | 9.421 ± 0.200 | 18 |
| 11.69 ± 0.20 | 7.562 ± 0.129 | 100 |
| 12.75 ± 0.20 | 6.940 ± 0.108 | 18 |
| 12.81 ± 0.20 | 6.904 ± 0.107 | 23 |
| 13.36 ± 0.20 | 6.622 ± 0.099 | 22 |
| 14.41 ± 0.20 | 6.141 ± 0.085 | 37 |
| 16.05 ± 0.20 | 5.517 ± 0.068 | 53 |
| 16.22 ± 0.20 | 5.459 ± 0.067 | 97 |
| 16.95 ± 0.20 | 5.226 ± 0.061 | 42 |
| 19.54 ± 0.20 | 4.540 ± 0.046 | 66 |
| 19.68 ± 0.20 | 4.507 ± 0.045 | 35 |
| 21.14 ± 0.20 | 4.199 ± 0.039 | 89 |
| 22.18 ± 0.20 | 4.005 ± 0.036 | 50 |
| 22.48 ± 0.20 | 3.952 ± 0.035 | 43 |
| 22.67 ± 0.20 | 3.919 ± 0.034 | 30 |
| 22.82 ± 0.20 | 3.893 ± 0.034 | 35 |
| 26.31 ± 0.20 | 3.385 ± 0.025 | 51 |

Citrate Form A was analyzed by proton NMR, and the spectrum was consistent with a 1:1 Compound A citrate salt with minor residual EtOH present.

An overlay of the DSC and TGA thermograms for citrate Form A is shown in FIG. 4. Negligible weight loss was observed by TGA up to 160° C., consistent with an anhydrous/nonsolvated material. Stepwise weight loss of about 24 wt % between 160° C. and 250° C. corresponds with an endothermic event by DSC with an onset of 200° C., likely indicating concurrent melting and decomposition of the material.

Hot stage images for the material confirm a melt onset at approximately 193° C., slightly lower than the melt onset marked in the DSC thermogram in FIG. 4 (200° C.).

The DVS (Dynamic Vapor Sorption) isotherm, shown in FIG. 5, illustrates low kinetic hygroscopicity (about 0.11% total weight gain/loss between 5% and 95% RH).

Citrate Form A has several unexpected properties. It exhibited improved aqueous solubility by solvent addition (6 mg/mL) as compared to Free Base Form A and showed no signs of disproportionation at the 6 mg/mL concentration for up to ~1 month. It has improved physical stability under a variety of conditions, and showed no deliquescence upon stressing the salt at ~97% RH for 14 days. Furthermore, the unit cell volume obtained from the XRPD indexing solution is consistent with an anhydrous/non-solvated 1:1 Compound A citrate salt.

Example 6. Compound A Citrate Form B

Citrate Form B consists of a likely monohydrate of a 1:1 Compound A citrate salt and was generated from a scale-up of the citrate salt. The sample was analyzed by XRPD (with indexing) and proton NMR.

The XRPD pattern for citrate Form B (FIG. 6) was successfully indexed, indicating the sample consists primarily or exclusively of a single crystalline phase. The unit cell volume is consistent with a 1:1 Compound A citrate salt and could accommodate up to 1 mole of water.

The XRPD pattern for citrate Form B was peak picked, and lists of observed and prominent peaks are shown in Tables 5 and 6, respectively.

TABLE 5

List of observed XRPD peaks for Citrate Form B

| °2θ | d space (Å) | Intensity (%) |
|---|---|---|
| 5.71 ± 0.20 | 15.467 ± 0.541 | 13 |
| 8.42 ± 0.20 | 10.499 ± 0.249 | 39 |
| 9.91 ± 0.20 | 8.917 ± 0.179 | 7 |
| 10.45 ± 0.20 | 8.463 ± 0.162 | 17 |
| 11.30 ± 0.20 | 7.824 ± 0.138 | 50 |
| 12.41 ± 0.20 | 7.124 ± 0.114 | 18 |
| 12.93 ± 0.20 | 6.840 ± 0.105 | 32 |
| 13.82 ± 0.20 | 6.403 ± 0.092 | 11 |
| 14.62 ± 0.20 | 6.055 ± 0.082 | 8 |
| 15.12 ± 0.20 | 5.853 ± 0.077 | 3 |
| 16.15 ± 0.20 | 5.484 ± 0.067 | 100 |
| 16.54 ± 0.20 | 5.356 ± 0.064 | 9 |
| 16.69 ± 0.20 | 5.309 ± 0.063 | 9 |
| 16.90 ± 0.20 | 5.241 ± 0.062 | 37 |
| 17.22 ± 0.20 | 5.145 ± 0.059 | 26 |
| 17.55 ± 0.20 | 5.049 ± 0.057 | 13 |
| 18.08 ± 0.20 | 4.904 ± 0.054 | 41 |
| 18.77 ± 0.20 | 4.723 ± 0.050 | 58 |
| 19.29 ± 0.20 | 4.597 ± 0.047 | 15 |
| 19.63 ± 0.20 | 4.518 ± 0.046 | 5 |
| 19.93 ± 0.20 | 4.452 ± 0.044 | 22 |
| 20.18 ± 0.20 | 4.398 ± 0.043 | 15 |
| 21.01 ± 0.20 | 4.226 ± 0.040 | 18 |
| 21.33 ± 0.20 | 4.163 ± 0.039 | 10 |
| 21.80 ± 0.20 | 4.074 ± 0.037 | 5 |
| 23.04 ± 0.20 | 3.858 ± 0.033 | 64 |
| 23.75 ± 0.20 | 3.743 ± 0.031 | 4 |
| 24.13 ± 0.20 | 3.685 ± 0.030 | 2 |
| 24.52 ± 0.20 | 3.628 ± 0.029 | 5 |
| 25.02 ± 0.20 | 3.555 ± 0.028 | 26 |
| 25.50 ± 0.20 | 3.491 ± 0.027 | 9 |
| 26.01 ± 0.20 | 3.423 ± 0.026 | 35 |
| 26.27 ± 0.20 | 3.390 ± 0.025 | 17 |
| 26.51 ± 0.20 | 3.360 ± 0.025 | 8 |
| 27.44 ± 0.20 | 3.247 ± 0.023 | 10 |
| 27.76 ± 0.20 | 3.211 ± 0.023 | 19 |
| 28.32 ± 0.20 | 3.149 ± 0.022 | 3 |
| 28.63 ± 0.20 | 3.115 ± 0.021 | 13 |
| 29.55 ± 0.20 | 3.020 ± 0.020 | 10 |

TABLE 6

List of prominent XRPD peaks for Citrate Form B

| °2θ | d space (Å) | Intensity (%) |
|---|---|---|
| 5.71 ± 0.20 | 15.467 ± 0.541 | 13 |
| 8.42 ± 0.20 | 10.499 ± 0.249 | 39 |
| 10.45 ± 0.20 | 8.463 ± 0.162 | 17 |
| 11.30 ± 0.20 | 7.824 ± 0.138 | 50 |
| 12.41 ± 0.20 | 7.124 ± 0.114 | 18 |
| 12.93 ± 0.20 | 6.840 ± 0.105 | 32 |
| 16.15 ± 0.20 | 5.484 ± 0.067 | 100 |
| 16.90 ± 0.20 | 5.241 ± 0.062 | 37 |
| 17.22 ± 0.20 | 5.145 ± 0.059 | 26 |
| 18.08 ± 0.20 | 4.904 ± 0.054 | 41 |
| 18.77 ± 0.20 | 4.723 ± 0.050 | 58 |
| 19.93 ± 0.20 | 4.452 ± 0.044 | 22 |
| 21.01 ± 0.20 | 4.226 ± 0.040 | 18 |
| 23.04 ± 0.20 | 3.858 ± 0.033 | 64 |
| 25.02 ± 0.20 | 3.555 ± 0.028 | 26 |
| 26.01 ± 0.20 | 3.423 ± 0.026 | 35 |

Proton NMR of the sample confirms a 1:1 Compound A citrate salt with only minor residual ethanol present.

Karl Fischer data indicated that a sample containing citrate Form B contained approximately 3 wt % water. This amount of water correlates with a monohydrate of a 1:1 citrate salt.

Example 7. Tartrate Form A of Compound A

Tartrate Form A consists of a ~2:1:1 Compound A/acid/EtOH solvated Compound A tartrate salt. In one embodiment, the material resulted from a salt formation experiment with L-tartaric acid in EtOH as shown in Table 2.

The XRPD pattern of tartrate Form A (FIG. 7) was successfully indexed, indicating the sample consists primarily or exclusively of a single crystalline phase. The unit cell volume obtained from the indexing solution can accommodate a 2:1 Compound A tartrate salt with up to 2 moles EtOH present per mole of 2:1 salt.

A proton NMR spectrum for tartrate Form A is consistent with a 2:1 salt with 0.4 mole EtOH per mole of Compound A, indicating a ~2:1:1 Compound A/acid/EtOH stoichiometry.

An overlay of the DSC and TGA thermograms for tartrate Form A is shown in FIG. 8. A broad endotherm with a peak maximum at 78° C. and a shoulder peak at 95° C. in the DSC thermogram corresponds with about 5% weight loss between 23 and 115° C. by TGA, consistent with the loss of solvent. The magnitude of weight loss is consistent with ~1 mole EtOH per mole of 2:1 Compound A tartrate salt, consistent with the amount of EtOH measured by proton NMR. An additional weight loss step of about 4 wt % corresponds with an endothermic event with a peak maximum at 158° C., likely corresponding with concurrent melting, dissociation, and decomposition of the salt.

Example 8. Tartrate Form B and Form C of Compound A

Tartrate Form A was found to convert to a new form, designated as tartrate Form B upon vacuum drying at ~66° C. for 1 day. Similarities in XRPD peak positions between Form A (FIG. 9, top pattern) and Form B (FIG. 9, middle pattern) were noted, possibly indicating partial desolvation of Form A at those conditions and a mixture of materials.

Figure 9:
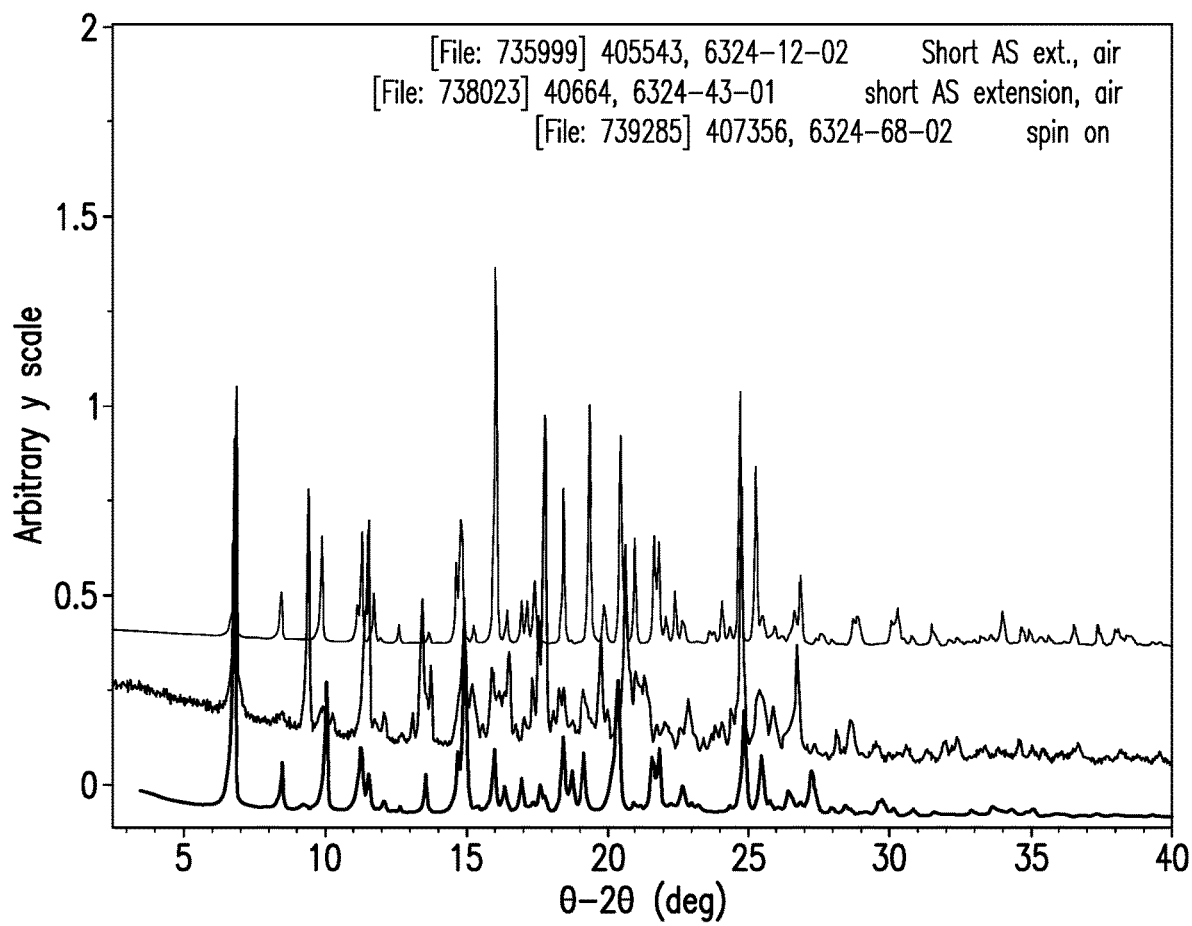
FIG. 9 is an XRPD overlay for tartrate salt Form A, Form B and Form C of Compound A.

Tartrate Form B was found to convert to Form C upon further vacuum drying at ~83-86° C. (FIG. 9, bottom pattern). Tartrate Form B was stressed at ~97% RH for 14 days and showed no signs of deliquescence.

Example 9. Tartrate Form D of Compound A

Figure 10:
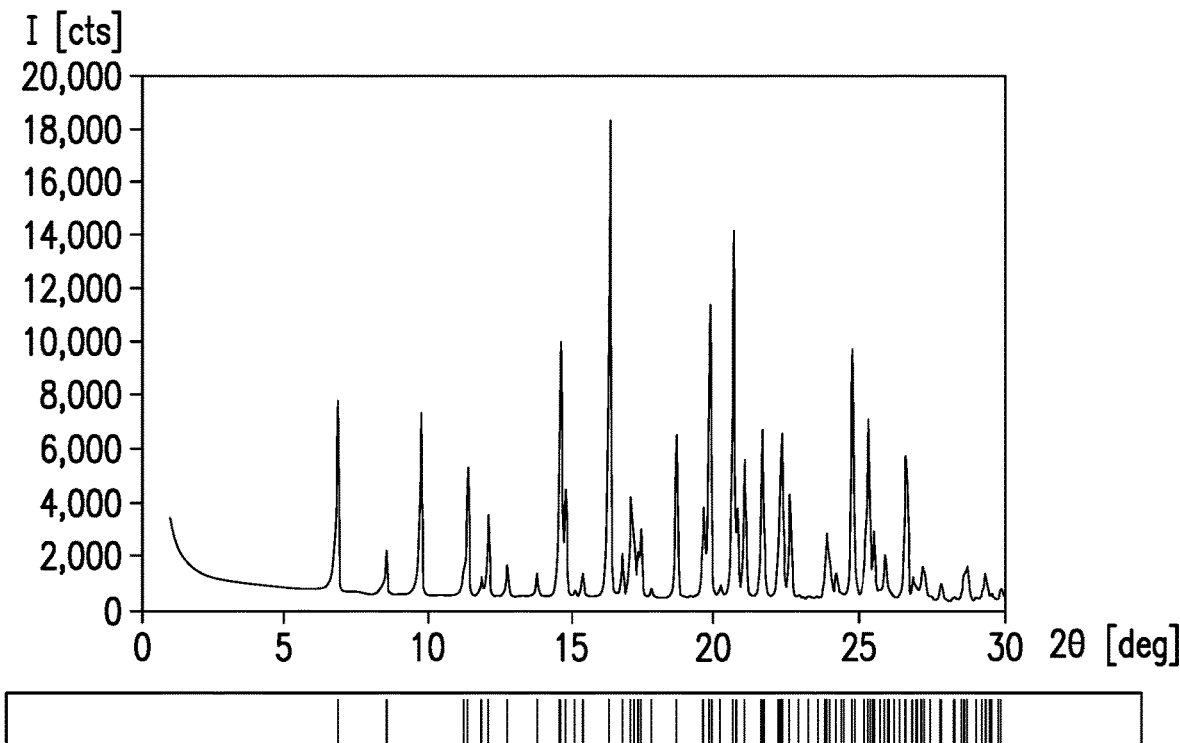
FIG. 10 is a characteristic XRPD pattern for tartrate salt Form D of Compound A.

Tartrate Form D consists of a ~2:1:1 Compound A/acid/EtOH solvated Compound A tartrate salt and initially resulted from a salt formation experiment in EtOH at ~70° C. (Table 2). The XRPD pattern was successfully indexed, indicating the material consists primarily or exclusively of a single crystalline phase (FIG. 10). The unit cell volume can accommodate a 2:1 Compound A tartrate salt with up to ~2 moles EtOH per mole of 2:1 salt.

Proton NMR of tartrate Form D is consistent with an EtOH solvated hemi-tartrate salt in a 2:1:1 Compound A/acid/EtOH molar ratio.

Example 10. Tartrate Form F of Compound A

Tartrate Form F consists of a ~2:1:3 Compound A/acid/water hydrated Compound A tartrate salt, although the water content may be variable. The material was reproducibly prepared by combining Compound A free base Form A with aqueous L-tartaric acid at ~50° C. (Table 7).

TABLE 7

Tartrate Form F of Compound A

| Intended Form/Scale | Conditions | Yield (%) | Technique | Results |
|---|---|---|---|---|
| Tartrate Form F ~1.0 g | 1) dissolve 1.5 molar eq. L-tartaric acid in water, add to API solids w/stirring at ~51° C. 2) add seeds of 1081 (Tartrate Form F), stir at ~51° C., 1 day 3) vac. filter while warm | 105% | Obs<br><br><br>OM<br>XRPD<br>KF | 1) opaque white suspension 2) opaque white suspension 3) white solids fines and aggregates, B/E Tartrate Form F, peak shifts 7.298% water (or 3.7 moles water per mole 2:1 salt) |

Tartrate Form F has improved aqueous solubility as compared to Compound A free base (2 mg/mL versus <1 mg/mL, respectively). This material exhibits some disproportionation in neat water, hygroscopicity, and a propensity to convert to a multitude of solvated forms. Tartrate Form F was characterized by XRPD (FIG. 11), proton NMR, DSC, TGA, hot stage microscopy, DVS, and Karl Fischer titration.

The unit cell volume from the indexing solution is consistent with a 2:1 Compound A tartrate salt with up to ~3 moles of water present (i.e. unit cell could accommodate 2:1:3 Compound A/acid/water). Minor peak shifts for select peaks were noted between multiple preparations, which may indicate variable water content.

An XRPD pattern for tartrate Form F was peak picked, and lists of observed and prominent peaks are shown in Tables 8 and 9, respectively.

TABLE 8

List of observed XRPD Peaks for Tartrate Form F

| °2θ | d space (Å) | Intensity (%) |
|---|---|---|
| 7.19 ± 0.20 | 12.288 ± 0.341 | 4 |
| 9.22 ± 0.20 | 9.588 ± 0.208 | 6 |
| 11.25 ± 0.20 | 7.857 ± 0.139 | 100 |
| 12.06 ± 0.20 | 7.332 ± 0.121 | 26 |
| 13.68 ± 0.20 | 6.467 ± 0.094 | 3 |
| 14.43 ± 0.20 | 6.133 ± 0.085 | 3 |
| 14.60 ± 0.20 | 6.063 ± 0.083 | 3 |
| 14.77 ± 0.20 | 5.992 ± 0.081 | 4 |
| 15.72 ± 0.20 | 5.632 ± 0.071 | 4 |
| 16.37 ± 0.20 | 5.410 ± 0.066 | 47 |
| 16.83 ± 0.20 | 5.263 ± 0.062 | 5 |
| 17.15 ± 0.20 | 5.167 ± 0.060 | 3 |
| 17.74 ± 0.20 | 4.994 ± 0.056 | 40 |
| 18.51 ± 0.20 | 4.790 ± 0.051 | 21 |
| 18.73 ± 0.20 | 4.734 ± 0.050 | 53 |
| 19.92 ± 0.20 | 4.453 ± 0.044 | 10 |
| 20.03 ± 0.20 | 4.429 ± 0.044 | 14 |

TABLE 8-continued

List of observed XRPD Peaks for Tartrate Form F

| °2θ | d space (Å) | Intensity (%) |
|---|---|---|
| 20.14 ± 0.20 | 4.406 ± 0.043 | 18 |
| 20.61 ± 0.20 | 4.305 ± 0.041 | 2 |
| 21.69 ± 0.20 | 4.095 ± 0.037 | 20 |
| 22.29 ± 0.20 | 3.985 ± 0.035 | 24 |
| 22.67 ± 0.20 | 3.920 ± 0.034 | 47 |
| 22.98 ± 0.20 | 3.867 ± 0.033 | 7 |
| 23.29 ± 0.20 | 3.816 ± 0.032 | 4 |
| 23.64 ± 0.20 | 3.760 ± 0.031 | 7 |
| 24.23 ± 0.20 | 3.670 ± 0.030 | 6 |
| 24.52 ± 0.20 | 3.627 ± 0.029 | 6 |
| 24.90 ± 0.20 | 3.573 ± 0.028 | 5 |
| 25.24 ± 0.20 | 3.525 ± 0.027 | 3 |
| 25.42 ± 0.20 | 3.501 ± 0.027 | 3 |
| 25.86 ± 0.20 | 3.443 ± 0.026 | 4 |
| 26.10 ± 0.20 | 3.411 ± 0.026 | 4 |
| 26.52 ± 0.20 | 3.358 ± 0.025 | 32 |
| 26.84 ± 0.20 | 3.319 ± 0.024 | 31 |
| 27.25 ± 0.20 | 3.270 ± 0.024 | 5 |
| 27.57 ± 0.20 | 3.233 ± 0.023 | 2 |
| 28.03 ± 0.20 | 3.180 ± 0.022 | 11 |
| 28.64 ± 0.20 | 3.114 ± 0.021 | 2 |
| 29.16 ± 0.20 | 3.060 ± 0.021 | 8 |
| 29.43 ± 0.20 | 3.032 ± 0.020 | 4 |
| 29.85 ± 0.20 | 2.991 ± 0.020 | 12 |

TABLE 9

List of Prominent XRPD Peaks for Tartrate Form F

| °2θ | d space (Å) | Intensity (%) |
|---|---|---|
| 11.25 ± 0.20 | 7.857 ± 0.139 | 100 |
| 12.06 ± 0.20 | 7.332 ± 0.121 | 26 |
| 16.37 ± 0.20 | 5.410 ± 0.066 | 47 |
| 17.74 ± 0.20 | 4.994 ± 0.056 | 40 |
| 18.51 ± 0.20 | 4.790 ± 0.051 | 21 |
| 18.73 ± 0.20 | 4.734 ± 0.050 | 53 |
| 21.69 ± 0.20 | 4.095 ± 0.037 | 20 |
| 22.29 ± 0.20 | 3.985 ± 0.035 | 24 |
| 22.67 ± 0.20 | 3.920 ± 0.034 | 47 |
| 26.52 ± 0.20 | 3.358 ± 0.025 | 32 |
| 26.84 ± 0.20 | 3.319 ± 0.024 | 31 |

A proton NMR spectrum for tartrate Form F is consistent with a 2:1 Compound A tartrate salt.

Figure 12:
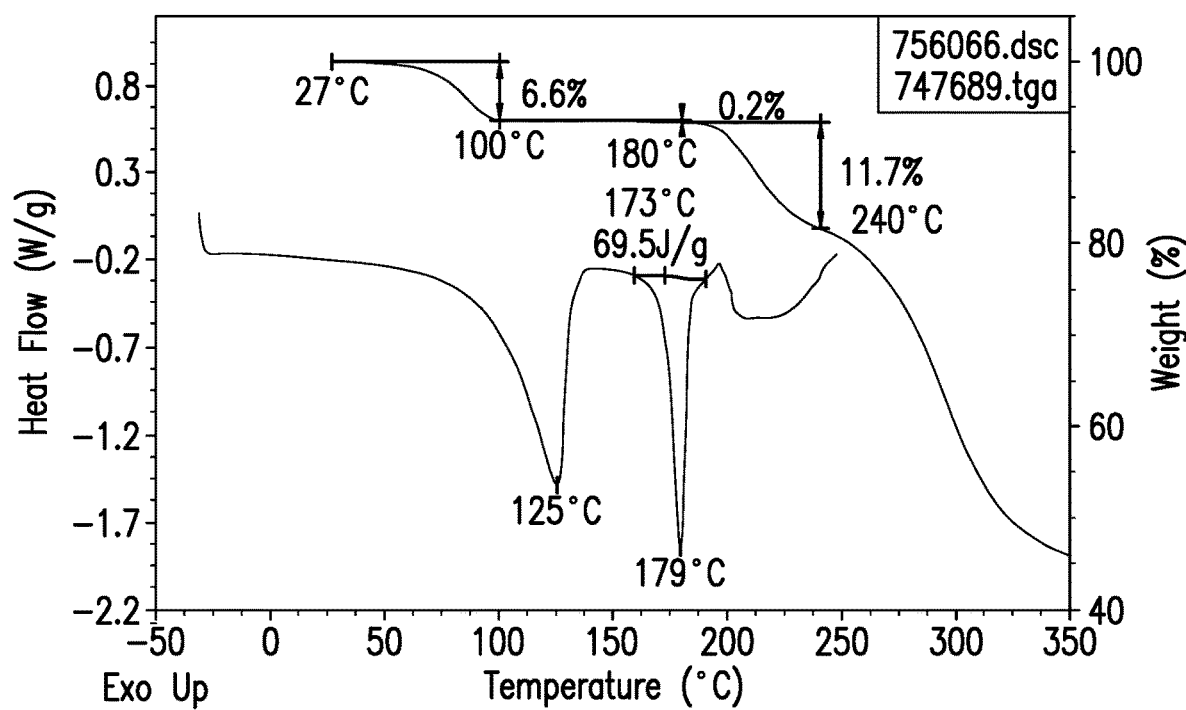
FIG. 12 is a DSC and TGA overlay for tartrate salt Form F of Compound A.

An overlay of the DSC and TGA thermograms for tartrate Form F is shown in FIG. 12. An initial weight loss step of about 6.6 wt % between 27-100° C. by TGA corresponds with a broad endotherm by DSC at 125° C., likely corresponding with the loss of solvent. The weight loss equates to ~3 moles water per mole of 2:1 salt, consistent with the amount of water allowed by the unit cell volume. Virtually no weight loss is noted between 100-180° C.

Hot stage photomicrographic analysis on tartrate Form F illustrated changes in birefringence noted between 70° C. and 98° C., corresponding with the stepwise weight loss and broad endotherm noted in the TGA and DSC data that likely indicate dehydration of the sample upon heating. Melting was observed between ~171° C. and 176° C., confirming that the sharp DSC endotherm at onset 173° C. corresponds with the melt of the dehydrated material.

Karl Fischer analysis of tartrate Form F indicated about 7.298% water, equivalent to approximately 3.7 moles water per mole of 2:1 salt. This water content is slightly higher than the ~3 moles of water indicated by the TGA weight loss and allowed by the unit cell volume.

A DVS isotherm for tartrate Form F is shown in FIG. 13. The material exhibited relatively small weight loss upon equilibration to 5% RH (0.29 wt %), indicating that the hydrate likely remained intact at the start of adsorption. Significant hygroscopicity was noted between 5% and 95% RH, with the sample gaining a total of about 4.23 wt %. Approximately half of the weight gain occurred gradually between 5% and 85% RH, while the other half occurred during the single step between 85% and 95% RH.

Although significant weight gain was observed from the DVS experiment, the hydrated material showed no signs of deliquescence at ~97% RH during the screen. The desorption profile mirrors the sorption profile with very little hysteresis observed. Total weight loss of about 4.25 wt % occurred between 95% and 5% RH, with approximately half of the weight loss occurring in one step between 95% and 85% RH. XRPD of the post-DVS sample indicated no form change.

Tartrate Form F exhibited improved aqueous solubility by solvent addition as compared to Compound A free base Form A, although disproportionation in neat water was observed to begin after 1 day.

Tartrate Form F was found to convert to a different tartrate form upon dehydration, and was converted back to Form F (with minor additional XRPD peaks) by stressing at ~97% RH.

Example 11. Tartrate Form G of Compound A

Figure 14:
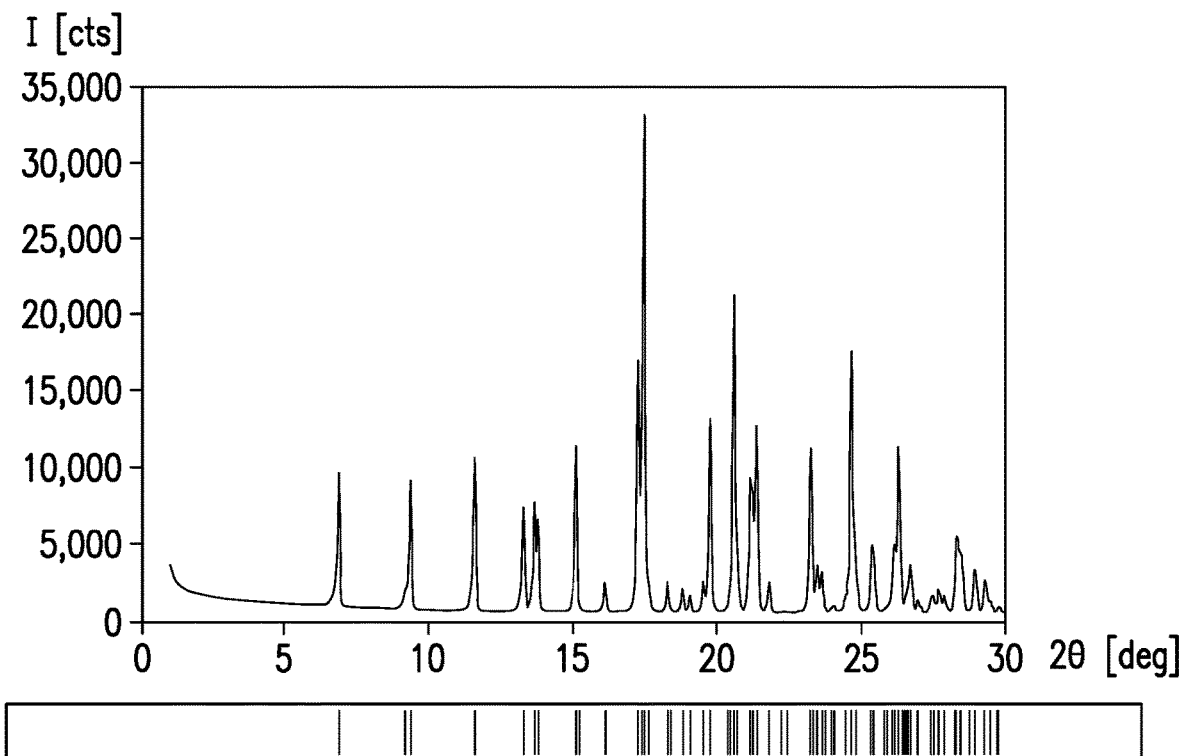
FIG. 14 is a characteristic XRPD pattern for tartrate salt Form G of Compound A.

Tartrate Form G consists of a ~2:1:2 Compound A/acid/ACN solvated tartrate salt and resulted from a slurry of tartrate Form F in ACN at ~76° C. The XRPD pattern of Form G is shown in FIG. 14, indicating the sample consists primarily or exclusively of a single crystalline phase. The unit cell volume obtained from the indexing solution could accommodate a 2:1 Compound A tartrate salt with up to 2 moles ACN per mole of 2:1 salt.

A proton NMR spectrum for tartrate Form G is consistent with a ~2:1:2 Compound A/tartrate/ACN solvated salt.

Example 12. Tartrate Form H of Compound A

Figure 15:
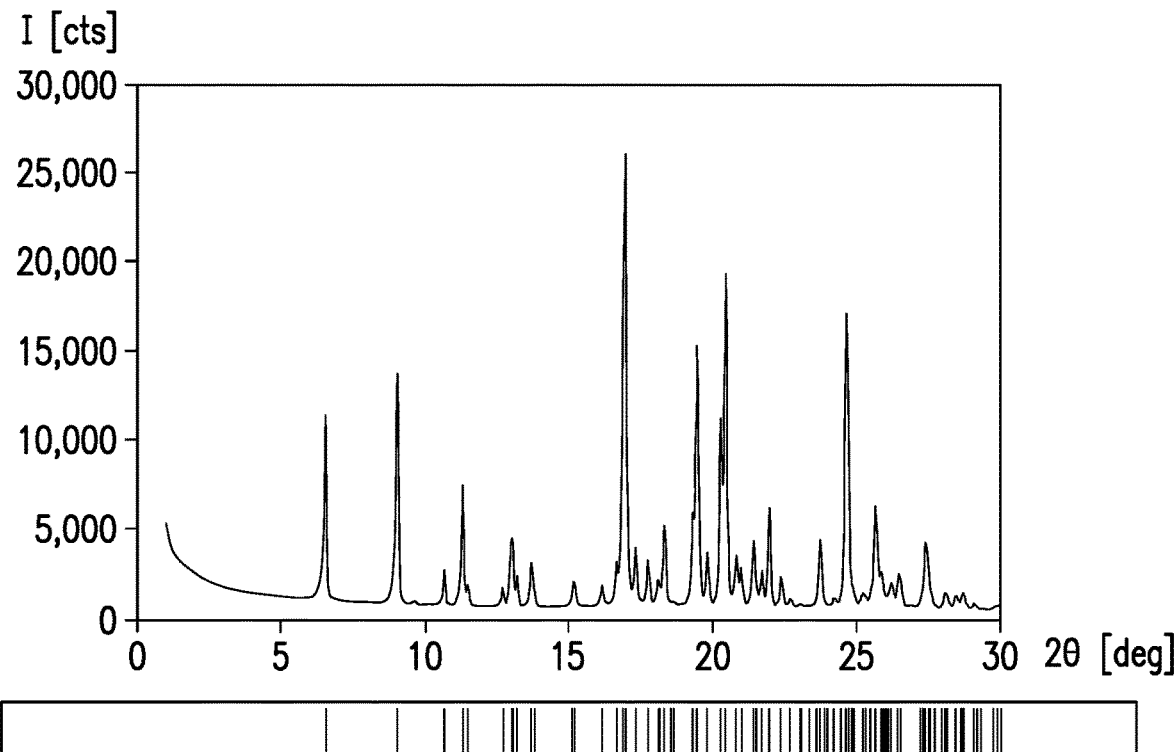
FIG. 15. is a characteristic XRPD pattern for tartrate salt Form H of Compound A.

Tartrate Form H consists of a ~2:1:1.5 Compound A/acid/THF solvated tartrate salt and is likely isostructurally solvated with IPA. The material resulted from slurry experiments starting with tartrate Form F in THF (resulted in Form H) and in IPA (resulted in a mixture of Form H and Form D). The XRPD pattern of Form H generated from THF was successfully indexed, indicating the material consisting primarily or exclusively of a single crystalline phase (FIG. 15). The unit cell parameters for Form H are similar to those of Tartrate Form F (a hydrate), possibly suggesting isostructural materials, although the XRPD patterns exhibit significant differences in peak positions and peak intensities. The unit cell volume of Form H is significantly larger than that of Form F and could accommodate up to 2 moles of THF per 2:1 Compound A/tartrate salt.

A proton NMR spectrum for the sample of Form H from THF is consistent with a ~2:1:1.5 Compound A/tartrate/THF solvated salt.

Considering the variety of solvents from which it was produced and the comparison of unit cell parameters, Form H may consist of a family of isostructural solvates of the hemi tartrate salt involving THF, IPA, and water.

Example 13. Milling Studies and Abbreviated Stable Form Screen

To evaluate possible citrate salt formation during formulation preparations, two milling experiments were conducted using free base Form A and one molar equivalent of citric acid, as shown in Table 10.

TABLE 10

Milling Experiments using Compound A Free Base Form A and Citric Acid

| API/Acid Molar Ratio | Conditions | Technique | Results |
|---|---|---|---|
| citric acid 1:1 | mill (dry) at 30 Hz for 3 × 10-min. cycles | Obs | white solids |
| | | OM | fines and aggregates, B/E |
| | | XRPD | FB Form A + citric acid |
| citric acid 1:1 | add water, mill at 30 Hz for 3 × 10-min. cycles | Obs | clear gel after first cycle, white solids after milling complete |
| | | OM | fines and aggregates, B/E |
| | | XRPD | Citrate Form A + minor FB Form A |

Figure 16:
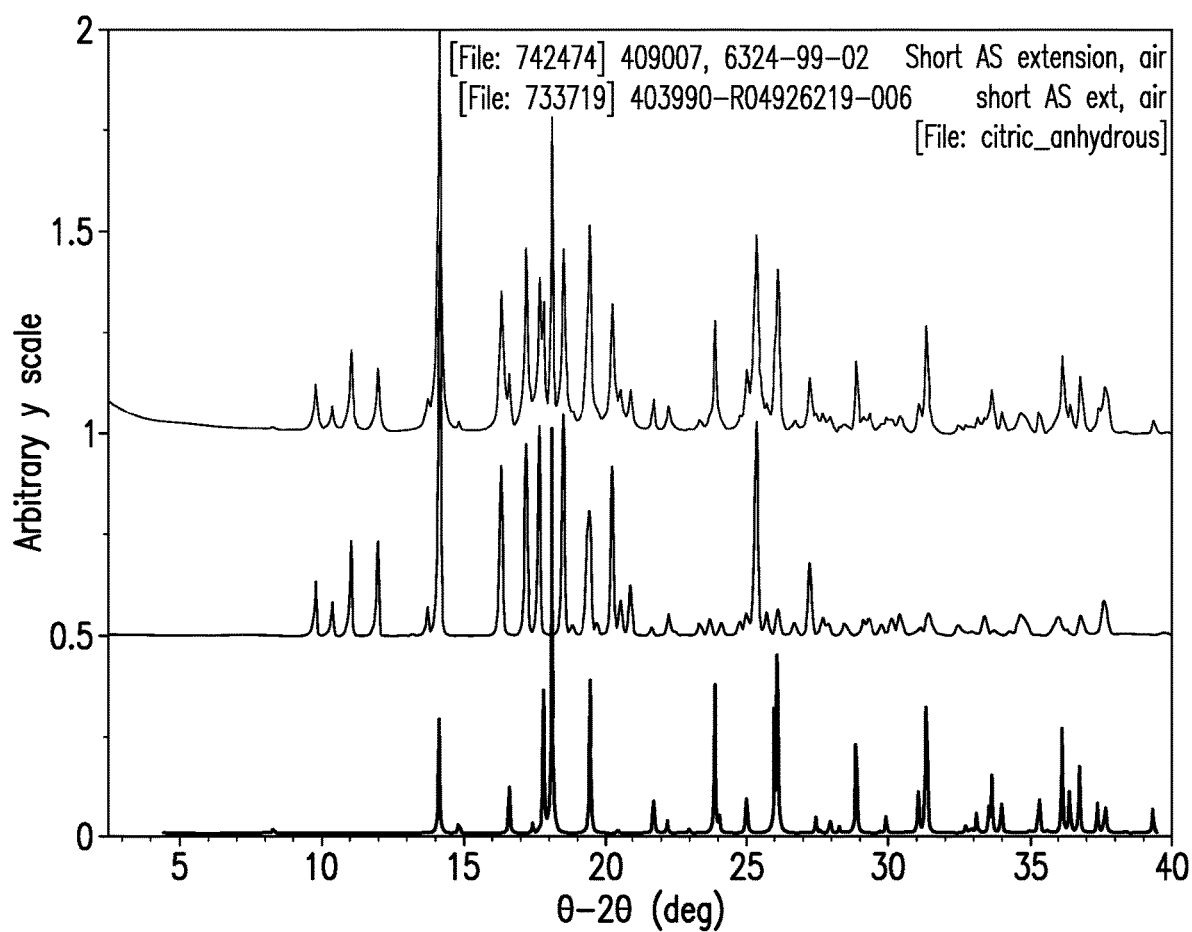
FIG. 16 is an XRPD overlay of dry grind of Compound A with molar equivalent of citric acid.
Figure 17:
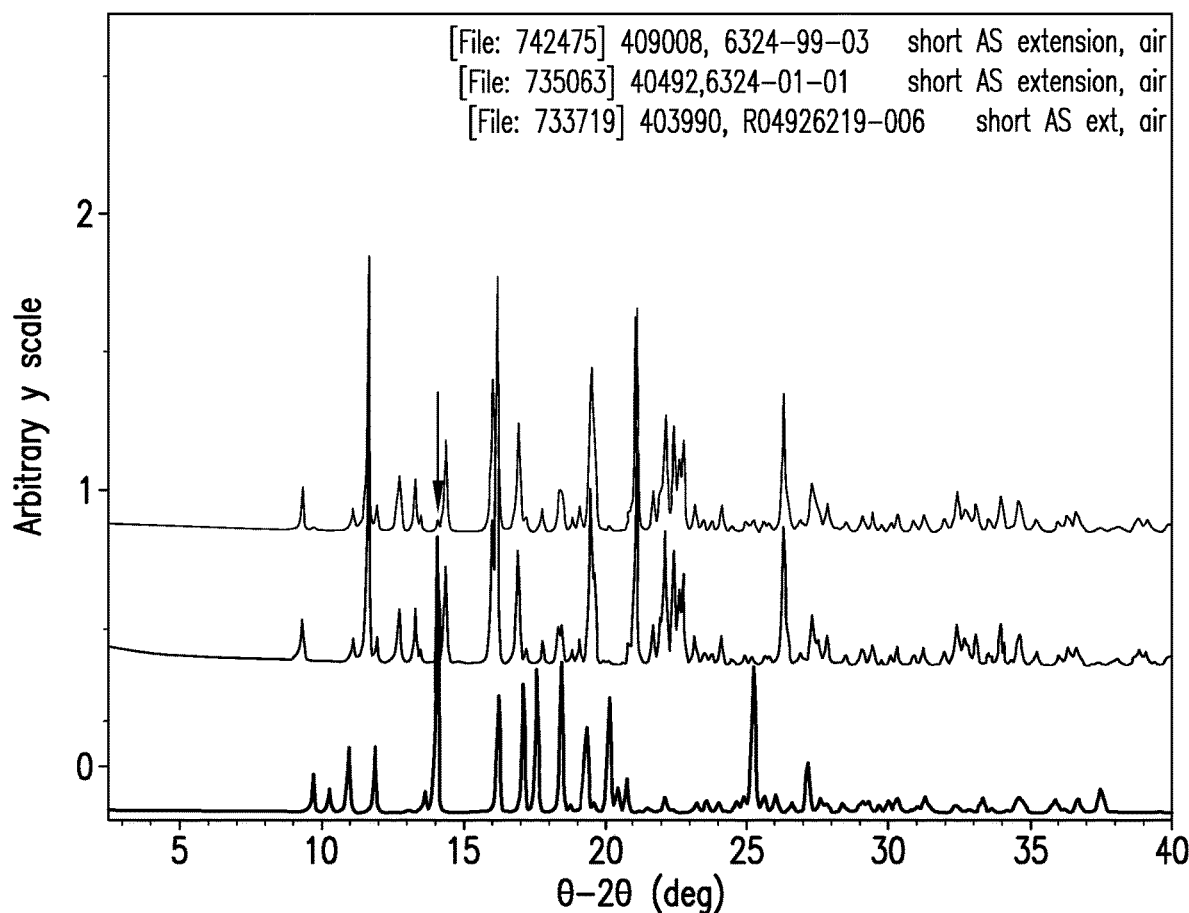
FIG. 17 is an XRPD overlay of wet grind of Compound A with molar equivalent of citric acid.

In one of the experiments, the components were milled together under dry conditions, while the other milling experiment involved the addition of a small amount of water to simulate wet granulation. The dry grind resulted in a physical mixture of free base and citric acid (FIG. 16), while the wet grind produced citrate Form A with a minor amount of unreacted free base (FIG. 17). These results indicate that a formulation process such as wet granulation would likely facilitate formation of a citrate salt in a formulation containing Compound A free base and citric acid. Additionally, salt formation in the formulation was confirmed by the XRPD analysis of several lots of formulated tablets, which exhibited peaks consistent with citrate salt forms in addition to the other crystalline components of the formulation.

Approximate solubility values for citrate Form A are shown in Table 11. Solubilities are calculated based on the total solvent used to give a solution; actual solubilities may be greater because of the volume of the solvent portions used or a slow rate of dissolution. Values are rounded to the nearest whole number. If dissolution did not occur as determined by visual assessment, the value is reported as "<". If dissolution occurred as determined by the visual assessment after the addition of the first aliquot, the value is reported as ">".

TABLE 11

Approximate Solubilities of Compound A Salts in Various Solvents at Ambient Temperature

| Salt Form | Solvent | Solubility (mg/mL) |
|---|---|---|
| Citrate Form A | acetone | <1 |
| | ACN | <1 |
| | chloroform | <1 |
| | DMSO | ~33 |
| | EtOAc/MeOH 50:50 (v/v) | 3 |
| | EtOH | <1 |
| | HFIPA | 10 |
| | MEK/DMSO 80:20 (v/v) | ~17 |
| | MeOH | ~9 |
| | TFE | <1 |
| | water | 6 |
| | acetone/water 50:50 (v/v) | 30 |
| | IPA/water 90:10 (v/v) | 1 |
| | THF/water 70:30 (v/v) | 44 |
| Tartrate Form F | acetone | 2 |
| | ACN | 1 |
| | chloroform | <1 |
| | EtOAc | <1 |
| | EtOH | <1 |
| | IPA | <1 |
| | MEK | 1 |
| | MeOH | 10 |
| | THF | 4 |
| | water | 2 |
| | acetone/water 50:50 (v/v) | 8 |
| | EtOH/water 80:20 (v/v) | 3 |
| | MeOH/water 40:60 (v/v) | ~6$^{Error!\ Bookmark\ not\ defined.}$ |

Citrate Form A exhibited low to limited solubility in most organic solvent systems, with the highest solubility values noted in DMSO (~33 mg/mL), HFIPA (~10 mg/mL), MeOH (~9 mg/mL), and water (6 mg/mL). These values facilitated the selection of solvent systems for use in the stable form screen. Solvent mixtures were explored to find optimal solubility values for long-term slurry experiments.

Twelve slurry experiments were set up using citrate Form A in a variety of organic solvent systems and in neat water (Table 12). All solvent systems were explored at room temperature (RT), and additional sub-ambient slurries were set up in MeOH and in water.

TABLE 12

Abbreviated Stable Form Screen of Compound A Citrate Form A

| Solvent System | Conditions | Technique | Results |
|---|---|---|---|
| acetone | 1) slurry, RT, 24 days 2) vac. filter | Obs | 1) clear liquid phase, white solids 2) white solids |
| | | OM | fines and aggregates, no B/E |
| | | XRPD | Citrate Form A |
| ACN | 1) slurry, RT, 24 days 2) vac. filter | Obs | 1) clear liquid phase, white solids 2) white solids |
| | | OM | fines and aggregates, partial B/E |
| | | XRPD | Citrate Form A |
| EtOAc/MeOH 50:50 | 1) slurry, RT, 24 days 2) vac. filter | Obs | 1) clear liquid phase, white solids 2) white solids |
| | | OM | fines and aggregates, partial B/E |
| | | XRPD | Citrate Form A |

TABLE 12-continued

Abbreviated Stable Form Screen of Compound A Citrate Form A

| Solvent System | Conditions | Technique | Results |
|---|---|---|---|
| EtOH | 1) slurry, RT, 24 days<br>2) vac. filter | Obs | 1) clear liquid phase, white solids<br>2) white solids |
| | | OM | fines and aggregates, no B/E |
| | | XRPD | Citrate Form A |
| HFIPA | 1) slurry, RT, 4 days<br>2) add solids, slurry, RT, 20 days more<br>3) vac. filter (0.2 μm PTFE) | Obs | 1) very small amt. solids remaining<br>2) clear liquid phase, small amt. white solids on vial at solvent line<br>3) no solids collected, filtrate became very viscous and evaporated to very small amt. (could not be recovered) |
| MEK | 1) slurry, RT, 24 days<br>2) vac. filter | Obs | 1) clear liquid phase, white solids<br>2) white solids |
| | | OM | fines and aggregates, partial B/E |
| | | XRPD | Citrate Form A |
| MeOH | 1) slurry, RT, 25 days<br>2) vac. filter | Obs | 1) clear liquid phase, white solids<br>2) white solids |
| | | OM | fines and aggregates, partial B/E |
| | | XRPD | Citrate Form A |
| MeOH | 1) slurry, 2-8° C., 25 days<br>2) vac. filter while cool | Obs | 1) opaque white suspension<br>2) white solids |
| | | OM | fines and aggregates, partial B/E |
| | | XRPD | Citrate Form A |
| TFE | 1) slurry, RT, 25 days<br>2) vac. filter | Obs | 1) opaque white suspension<br>2) white solids |
| | | OM | fines and aggregates, B/E |
| | | XRPD | Citrate Form A |
| THF | 1) slurry, RT, 25 days<br>2) vac. filter | Obs | 1) clear liquid phase, white solids<br>2) white solids |
| | | OM | fines and aggregates, partial B/E |
| | | XRPD | Citrate Form A |
| water | 1) slurry, RT, 25 days<br>2) vac. filter | Obs | 1) opaque white suspension<br>2) damp white solids |
| | | OM | fines and aggregates, B/E |
| | | XRPD | Citrate Form A |
| water | 1) slurry, 2-8° C., 25 days<br>2) vac. filter while cool | Obs | 1) opaque white suspension<br>2) slightly damp white solids |
| | | OM | fines and aggregates, B/E |
| | | XRPD | Citrate Form A |

All of the slurries resulted in citrate Form A. The salt exhibited measurable solubility by solvent addition in many of the solvent systems employed, which would facilitate the kinetics of form conversion if a more stable form existed. Additionally, the slurries were all allowed to stir for 24-25 days, an extensive duration that would have likely provided adequate time for conversion to a more stable form if one existed. Considering these factors, citrate Form A is likely the most thermodynamically stable anhydrous form of the citrate salt at the conditions tested.

Example 14. Preparations of Select Compound A Salts

In addition to the processes described above, various salts of Compound A can be prepared using the following procedures.

Compound A Citrate Form A—

Compound A free base Form A solids (1.1957 g) were combined with EtOH (70 mL) at a concentration of 17 mg/mL, resulting in a slurry. Aqueous 1 M citric acid solution (1.2 molar equivalents, 4.06 mL) was added to the slurry, and no visible change was noted. The mixture was left to stir at ambient temperature for 12 days, resulting in an opaque white suspension. Solids were collected on a paper filter by vacuum filtration and air dried on the filter under reduced pressure for approximately 4 minutes. The solids were transferred to a clean vial, resulting in about 98% yield.

Alternatively, Compound A solids (5.5987 g) were combined with EtOH (330 mL) at a concentration of 17 mg/mL, resulting in a slurry. Aqueous 1 M citric acid solution (1.2 molar equivalents, 19 mL) was added to the slurry, and no visible change was noted. Seeds of citrate Form A were added at 1% seed load (55.6 mg), and no visible change was noted. The mixture was left to stir at ambient temperature for 3 days, resulting in an opaque white suspension. Solids were collected on a paper filter by vacuum filtration and air dried on the filter under reduced pressure for approximately 10 min and the solids were transferred to a clean vial.

Compound A Tartrate Form F—

Compound A free base Form A solids (1.0022 g) were combined with 1.5 molar equivalents of aqueous L-tartaric acid (0.6319 g acid dissolved in 12 mL water) with stirring at ~51° C., resulting in an opaque white suspension. A small amount of seeds of tartrate Form F were added and the mixture was allowed to stir at ~51° C. for 1 day, resulting in an opaque white suspension. Solids were collected on a paper filter by vacuum filtration while still warm and air dried on the filter under reduced pressure for about 4 min.

Example 15. Crystallization Techniques

The following crystallization techniques used in the salt screening and/or preparation processes are described in more detail below.

Fast Cool (FC)—

Saturated solutions of given Compound A salt materials were prepared in a given solvent at an elevated temperature. The vial was capped and placed on the lab bench to quickly cool to ambient temperature. Solids were isolated and analyzed.

Milling—

Weighed amounts of given Compound A materials (e.g. Compound A free base with given acids) were transferred to an agate milling container. An agate milling ball and a small amount of a given solvent (if specified) were added to the container, which was then attached to a Retsch mill. The mixture was milled for three 10-minute cycles at 30 Hz, and the solids were scraped down the walls of the jar between cycles. The resulting solids were transferred to a clean vial and analyzed.

Slurry Experiments—

Suspensions of given Compound A materials (e.g. prepared salts or mixtures of Compound A free base with various acids) were prepared by adding enough solids to a given solvent or solvent system at the stated temperature such that undissolved solids were present. Where specified, seeds of select materials were added. The mixture was then agitated (typically by stirring or oscillation) in a sealed vial at the stated conditions for an extended period of time. Solids were isolated and analyzed.

Relative Humidity Stressing—

Solids of given Compound A materials were transferred to a vial, which was then uncapped and placed inside ajar containing a saturated aqueous potassium sulfate solution for ~97% RH. Relative humidity stressing experiments were conducted at ambient temperature.

Vacuum Filtration—

Solids were collected on paper or nylon filters by vacuum filtration and air dried on the filters under reduced pressure briefly before transferring to a vial.

XRPD Peak Identification—

FIGS. 1 through 3, 6 through 7, 9 through 11, and 14 through 17 in this disclosure contain x-ray diffraction patterns, some with labeled peaks and/or tables with peak lists. Peak within the range of up to about 30° 2θ were selected. Rounding algorithms were used to round each peak to the nearest 0.01° 2θ. The location of the peaks along the x-axis (° 2θ) in both the figures and the lists were determined using proprietary software (TRIADSTM v2.0) and rounded to two significant figures after the decimal point. Peak position variabilities are given to within ±0.2° 2θ based upon recommendations outlined in the USP discussion of variability in x-ray powder diffraction.

For d-space listings, the wavelength used to calculate d-spacings was 1.5405929 Å, the Cu-Kα1 wavelength. Variability associated with d-spacing estimates was calculated from the USP recommendation, at each d-spacing, and provided in the respective data tables.

Per USP guidelines, variable hydrates and solvates may display peak variances greater than 0.2° 2θ and therefore peak variances of 0.2° 2θ are not applicable to these materials.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks".

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a Compound Against all other known crystalline polymorphs of that compound to within ±0.2° 2θ. Not all crystalline polymorphs of a compound necessarily have at least one characteristic peak.

Example 16. Instrumental Techniques

The instrumental techniques used in the salt screening and characterization processes are described in more detail below.

Differential Scanning calorimetry (DSC)—

DSC was performed using a TA Instruments Q2000 differential scanning calorimeter. Temperature calibration was performed using NIST-traceable indium metal. A sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this disclosure. The method code on the thermogram is an abbreviation for the start and end temperature as well as the heating rate; e.g., –30-250-10 means "from –30° C. to 250° C., at 10° C./min". The following table summarizes the abbreviations used in each image for pan configurations:

| Abbreviation (in comments) | Meaning |
| --- | --- |
| T0C | Tzero crimped pan |
| HS | Lid hermetically sealed |
| HSLP | Lid hermetically sealed and perforated with a laser pinhole |
| C | Lid crimped |
| NC | Lid not crimped |

Dynamic Vapor Sorption (DVS)—

Dynamic vapor sorption (DVS) data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Hot Stage Microscopy—

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20' 0.40 N. A. long working distance objective with crossed polarizers and a first order red compensator. Images were captured using SPOT software (v. 4.5.9).

Optical Microscopy—

Samples were observed under a Wolfe optical microscope with crossed polarizers at either 2' or 4' objectives or under a Leica stereomicroscope with a first order red compensator with crossed polarizers at 0.8× to 10× objectives.

Solution $^1$H NMR Spectroscopy—

The solution NMR spectrum was acquired with an Agilent DD2-400 spectrometer. The sample was prepared by dissolving approximately 5-10 mg of sample in DMSO-d6 containing TMS. The data acquisition parameters are displayed in the first plot of the spectrum in the Data section of this disclosure. The residual peak from incompletely deuterated DMSO is at approximately 2.50 ppm. The relatively broad peak at approximately 3.3 ppm, if present, is due to water.

Alternatively, data acquisition parameters are displayed on the first page of each spectrum in the Data section of this disclosure. The residual peak from incompletely deuterated DMSO is at approximately 2.50 ppm. The relatively broad peak at approximately 3.3 ppm, if present, is due to water.

Thermogravimetry (TGA)—

TG analyses were performed using a TA Instruments Discovery thermogravimetric analyzer. Temperature calibration was performed using nickel and AlumelÖ. Each sample was placed in an aluminum pan and inserted into the TG furnace. The furnace was heated under a nitrogen purge. The data acquisition parameters are displayed above each thermogram in the Data section of this disclosure. The method code on the thermogram is an abbreviation for the start and end temperature as well as the heating rate; e.g., 25-350-10 means "from 25° C. to 350° C., at 10° C./min".

X-ray Powder Diffraction (XRPD)—

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this disclosure including the divergence slit (DS) before the mirror and the incident-beam antiscatter slit (SS), if applicable.

Alternatively, XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are displayed above the image in the Data section of this disclosure including the divergence slit (DS) and the incident-beam SS.

Example 17: Preparation of Tablets with Compound A and Tartaric Acid

Two batches of tablets containing Compound A and tartaric acid were made using wet granulation following same procedures. Batch formula and preparation procedure were provided in Table 13 which shows the amounts of ingredients used in the formulations and subsequent compositions of tablets in batch 1 and batch 2.

TABLE 13

| Ingredient | Target formulation Wt/Tablet mg | %/Tablet | Batch 1 Wt/Batch gram | Batch 2 Wt/Batch gram |
|---|---|---|---|---|
| Compound A (IG) | 150 | 37.5 | 3 | 11.25 |
| Tartaric acid (IG) | 100 | 25 | 2 | 7.5 |
| Ac-di-sol (IG) | 10 | 2.5 | 0.2 | 0.75 |
| HPMC, 2910 E5 (IG) | 10 | 2.5 | 0.2 | 0.75 |
| Ac-di-sol (EG) | 10 | 2.5 | 0.2 | 0.75 |
| Avicel PH102 (EG) | 116 | 29 | 2.32 | 8.7 |
| Magnesium Stearate (EG) | 4 | 1 | 0.08 | 0.3 |
| Total | 400 | 100 | 8 | 30 |

IG—intragranular;
EG—Extragranular

Preparation procedure for making tablets batch 1 and batch 2:

1. All of the intragranular ingredients (IG) were weighed and mixed in a mortar using a spatula for at least 1 minute.
2. While mixing, water was added slowly in 5% increments until the appropriate granulation wetness was achieved. The total amount water added was around 20% w/w of the mixture of ingredients.
3. The wet mass was passed through an 18 mesh screen and the granules were collected and dried in an oven overnight at 35° C.
4. The granules collected were measured and the amounts of each of the extragranular ingredients (EG) were calculated accordingly.
5. The extragranular Ac-di-sol and Avicel were weighed and mixed with the granules for 2 minutes.
6. The magnesium stearate was weighed and mixed with the blend of step 5 for 0.5 minutes.
7. The resulting blend was compressed to give a tablet using ⅜" standard round concave tooling at 400 mg tablet weight. The blend weight range for compression was from 390 to 410 mg. The compression forces were adjusted to achieve 10 to 15 kp hardness.

Example 18—Preparation of Tablets with Compound A and Citric Acid

Tablets containing Compound A and citric acid were manufactured using wet granulation following a similar procedure as with the tartaric acid tablets in Example 16. Batch formula and preparation procedure were provided in Table 14 which shows the amounts of ingredients used in the formulation and subsequent composition of tablets in batch 1.

TABLE 14

| | Target formulation | | Batch 1 |
|---|---|---|---|
| Ingredient | Wt/Tablet mg | %/Tablet | Wt/Batch gram |
| Compound A (IG) | 50 | 33.33 | 2000 |
| Citric acid (IG) | 45 | 30.00 | 1800 |
| Lactose (IG) | 26.95 | 17.96 | 1078 |
| Acdisol (IG) | 3.5 | 2.33 | 140 |
| HPMC*, 2910 E5 (IG) | 4.5 | 3.0 | 180 |

TABLE 14-continued

| | Target formulation | | Batch 1 |
|---|---|---|---|
| Ingredient | Wt/Tablet mg | %/Tablet | Wt/Batch gram |
| Acdisol (EG) | 4.5 | 3.0 | 160 |
| Avicel PH102 (EG) | 15 | 10 | 600 |
| magnesium Stearate (EG) | 1.05 | 0.7 | 42 |
| Tablet Core Weight | 150 | 100 | 6000 |
| Tablet coating | 4 | | 270 |
| Total | 154 | | 6270 |

IG—intragranular;
EG—Extragranular

Preparation procedure manufacturing tablets batch 1:

1. All of the intragranular ingredients (IG) were weighed and mixed in a granulator for at least 1 minute.
2. While mixing, water was added slowly in increments until the appropriate granulation wetness was achieved. The total amount water added was around 20% w/w of the mixture of ingredients.
3. The wet mass was dried overnight at 25° C., then in a fluid bed drier for approximately 40 minutes at 50° C.
4. The granules were collected, milled, and were measured and the amounts of each of the extragranular ingredients (EG) were calculated accordingly.
5. The extragranular Acdisol and Avicel were weighted and mixed with the granules for 2 minutes.
6. The magnesium stearate was weighed and mixed with the blend of step 5 for 0.5 minutes.
7. The resulting blend was compressed to give a tablet using 7 mm standard round concave tooling at 150 mg tablet weight. The compression forces were adjusted to achieve 10 to 15 kp hardness.
8. The resulting tablet cores were coated with an aqueous Opadry in a pan coater until approximately a 3 percent weight gain was achieved.

Example 19—Dissolution of Tablets with Compound A and Citric or Tartaric Acids at pH 6.8

The tablets used in this example were prepared using the procedures outlined in Examples 17 and 18. The tablets were made to a total weight of ~150 mg with 50 mg of Compound A.

Table 15 shows the dissolution rates of tablets containing Compound A and lactose with or without citric acid, or tartaric acid in 500 mL of 50 mM phosphate-buffered saline, pH 6.8. Each composition (citric acid, lactose and tartaric acid) were tested in three separate experiments.

TABLE 15

| | Dissolution Rates | | | | | | | | |
|---|---|---|---|---|---|---|---|---|---|
| Time, min | 50-mg Citric Tablets (n = 3) | | | 50-mg - Lactose Tablets (n = 3) | | | 50-mg - Tartaric Tablets (n = 3) | | |
| 7.5 | 19.00 | 21.30 | 19.80 | 2.50 | 2.70 | 2.90 | 33.50 | 24.80 | 24.10 |
| 15.0 | 21.90 | 25.50 | 24.40 | 3.20 | 3.30 | 3.60 | 40.40 | 31.80 | 28.80 |
| 22.5 | 24.60 | 28.50 | 27.20 | 3.70 | 3.90 | 4.00 | 43.90 | 34.70 | 32.70 |
| 30.0 | 27.10 | 30.90 | 28.30 | 4.00 | 4.00 | 4.50 | 47.60 | 37.90 | 34.20 |
| 45.0 | 28.80 | 33.60 | 31.80 | 4.40 | 4.60 | 5.80 | 51.00 | 41.60 | 38.20 |
| 60.0 | 36.90 | 43.10 | 39.80 | 5.70 | 5.80 | 6.20 | 63.40 | 49.50 | 48.10 |

Dissolution quoted for each sample of the experiments is in % of Compound A dissolved.

As can be seen from the results in Table 15, Compound A in the citric acid tablet and the tartaric acid tablet dissolved more readily than in the lactose tablet at pH 6.8.

Example 20—In Vivo Testing of Tablet with Compound A and Tartaric Acid

The tablets of batch 2 (Example 17, Table 13) were used to carry out this study. The tablets were administered orally to eleven dogs. Four dogs received pentagastrin (6 µg/kg) intramuscularly 30 minutes prior to the tablet. Four dogs received famotidine (40 mg/dog) orally 2 hours prior to the tablet. Three dogs received no pre-treatment.

Famotidine inhibits stomach acid production and is used to raise gastric pH (i.e. to make it more neutral). Pentagastrin stimulates the production of stomach acid and is used to reduce the gastric pH (i.e. to make it more acidic).

The dogs were fasted overnight and each dog received a single tablet containing 150 mg of Compound A. The dogs weighed approximately 10 kg each, the target dose rate was 15 mg/kg.

A similar prior study was carried out using a suspension of Compound A (i.e. with tartaric or citric acid) and the results of the present study are compared with the results of this prior study.

Samples of blood were collected pre-dose and at 0.083, 0.25, 0.5, 1, 2, 4, 6, 8, 24, 32, and 48 hours after dosing. The blood was centrifuged to obtain plasma, which was assayed for levels of Compound A by LC-MS and pharmacokinetic parameters were calculated. The pharmacokinetic parameters were reported on actual measured concentrations and also adjusted for the weight of each individual dog. Concentrations below the detection limit (BLQ) were considered to be zero for calculations.

Table 16 shows the mean pharmacokinetic parameters of Compound A in the tartaric acid tablet of batch 2 administered orally to dogs.

TABLE 16

| | Pre-treatment of Dogs | | |
|---|---|---|---|
| | Pentagastrin (n = 4) | Famotidine (n = 4) | No treatment (n = 3) |
| Cmax (µg/mL) | 6.07 | 6.35 | 9.73 |
| AUC 0-48 h (µg*h/mL) | 64.8 | 60.7 | 78.8 |

Dogs pre-treated with pentagastrin, famotidine, and those which had no pre-treatment had approximately equal group mean Cmax and AUC values (Table 16).

The results of this study suggest that the variability of Compound A absorption due to differences in gastrointestinal pH can be overcome by formulating Compound A in a tablet containing tartaric acid. It is hypothesized that this is due to the improved properties of the tartrate salt formed in the formulation containing tartaric acid.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope. Changes therein and other uses will occur to those skilled in the art, which are encompassed within the spirit of the present disclosure, are defined by the scope of the claims.

What is claimed is:

1. A crystalline citrate Form B of 5-(2,4-diamino-pyrimidin-5-yloxy)-4-isopropyl-2-methoxy-benzenesulfonamide characterized by having X-ray powder diffraction peaks at 2θ values of approximately 11.3, 16.2 and 23.0 degrees.

2. The crystalline citrate Form B of claim 1, further characterized by having an X-ray powder diffraction peak at 2θ value of approximately 5.7 degrees.

3. The crystalline citrate Form B of claim 2, further characterized by having an X-ray powder diffraction peak at 2θ value of approximately 8.4 degrees.

4. The crystalline citrate Form B of claim 3, further characterized by having an X-ray powder diffraction peak at 2θ value of approximately 18.8 degrees.

5. The crystalline citrate Form B of claim 4, further characterized by having an X-ray powder diffraction peak at 2θ value of approximately 25.0 degrees.

6. A crystalline citrate Form B characterized by having X-ray powder diffraction peaks at 2θ values of approximately 5.7, 8.4, 11.3, 16.2, 18.8, 23.0 and 25.0 degrees.

7. The crystalline citrate Form B of claim 1 further characterized by having an X-ray powder diffraction pattern substantially as depicted in FIG. 6.

8. A pharmaceutical composition comprising the crystalline citrate Form B of claim 1 and a pharmaceutically acceptable carrier.

9. A method of modulating a condition mediated by a P2X3 or P2X2/3 receptor, said method comprising administering an effective amount of the crystalline citrate Form B of claim 1 to a subject in need thereof.

10. The method of claim 9, wherein the condition mediated by a P2X3 or P2X2/3 receptor is selected from cough, chronic cough and urge to cough.

11. A crystalline tartrate Form F of 5-(2,4-diamino-pyrimidin-5-yloxy)-4-isopropyl-2-methoxy-benzenesulfonamide characterized by having X-ray powder diffraction peaks at 2θ values of approximately 11.3, 18.7, and 22.7 degrees.

12. The crystalline tartrate Form F of claim 11, further characterized by having X-ray powder diffraction peaks at 2θ values of approximately 12.1 and 17.7 degrees.

13. The crystalline tartrate Form F of claim 11, further characterized by having an X-ray powder diffraction pattern substantially as depicted in FIG. 11.

14. The crystalline tartrate Form F of claim 11, further characterized by having a TGA thermogram showing weight losses of about 6.6 wt % from 27° C. to 100° C., a further weight loss of about 11.7 wt % between 180° C. and 240° C.

15. The crystalline tartrate Form F of claim 11, further characterized by proton nuclear magnetic resonance (NMR) data showing a 2:1 Compound A to tartrate ratio.

16. The crystalline tartrate Form F of claim 11, further characterized by having a TGA thermogram substantially as depicted in FIG. 12.

17. A pharmaceutical composition comprising the crystalline tartrate Form F of claim 11 and a pharmaceutically acceptable carrier.

18. A method of modulating a condition mediated by a P2X3 or P2X2/3 receptor, said method comprising administering an effective amount of the crystalline tartrate Form F of claim 11 to a subject in need thereof.

19. The method of claim 18, wherein the condition mediated by a P2X3 or P2X2/3 receptor is selected from cough, chronic cough and urge to cough.

* * * * *